US010668052B2

(12) United States Patent
Duffield et al.

(10) Patent No.: US 10,668,052 B2
(45) Date of Patent: Jun. 2, 2020

(54) COMBINATIONS OF ISOMERS OF DIHYDROTETRABENAZINE

(71) Applicant: ADEPTIO PHARMACEUTICALS LIMITED, London (GB)

(72) Inventors: Andrew John Duffield, Berkhamsted (GB); Anant Pandya, Croydon (GB)

(73) Assignee: ADEPTIO PHARMACEUTICALS LIMITED, London (GB)

( * ) Notice: Subject to any disclaimer, the term of this patent is extended or adjusted under 35 U.S.C. 154(b) by 0 days.

(21) Appl. No.: 15/939,837

(22) Filed: Mar. 29, 2018

(65) Prior Publication Data

US 2018/0280361 A1  Oct. 4, 2018

Related U.S. Application Data

(60) Provisional application No. 62/515,940, filed on Jun. 6, 2017.

(30) Foreign Application Priority Data

Apr. 1, 2017  (GB) .................................. 1705306.7

(51) Int. Cl.
  *A61K 31/435*  (2006.01)
  *A61P 25/14*  (2006.01)
  *A61K 9/48*  (2006.01)
  *A61K 9/20*  (2006.01)

(52) U.S. Cl.
  CPC ............ *A61K 31/435* (2013.01); *A61P 25/14* (2018.01); *A61K 9/20* (2013.01); *A61K 9/48* (2013.01); *A61K 2300/00* (2013.01)

(58) Field of Classification Search
  CPC ........................... C07D 455/04; A61K 31/435
  See application file for complete search history.

(56) References Cited

U.S. PATENT DOCUMENTS

| | | | |
|---|---|---|---|
| 7,919,622 B2 | 4/2011 | Amarasinghe et al. | |
| 8,039,627 B2 | 10/2011 | Gano | |
| 2010/0087475 A1* | 4/2010 | Duffield ............... | C07D 455/06 514/294 |
| 2012/0003330 A1 | 1/2012 | Gant et al. | |
| 2018/0280359 A1 | 10/2018 | Duffield et al. | |
| 2018/0280360 A1 | 10/2018 | Duffield et al. | |
| 2018/0280374 A1 | 10/2018 | Duffield et al. | |
| 2018/0280375 A1 | 10/2018 | Duffield et al. | |
| 2019/0111035 A1 | 4/2019 | Duffield et al. | |

FOREIGN PATENT DOCUMENTS

| | | |
|---|---|---|
| CN | 102285984 A | 12/2011 |
| GB | 800969 A | 9/1958 |
| WO | 2005077946 A1 | 8/2005 |
| WO | 2006053067 A2 | 5/2006 |
| WO | 2007007105 A1 | 1/2007 |
| WO | 2007017654 A1 | 2/2007 |
| WO | 2008058261 A1 | 5/2008 |
| WO | 2009073677 A1 | 6/2009 |
| WO | 2010018408 A2 | 2/2010 |
| WO | 2010026436 A2 | 3/2010 |
| WO | 2011153157 A2 | 12/2011 |
| WO | 2014047167 A1 | 3/2014 |
| WO | 2015120110 A2 | 8/2015 |
| WO | 2015171802 A1 | 11/2015 |
| WO | 2016127133 A1 | 8/2016 |
| WO | 2016210180 A2 | 12/2016 |
| WO | 2017112857 A1 | 6/2017 |
| WO | 2018140092 A1 | 8/2018 |
| WO | 2018140093 A1 | 8/2018 |
| WO | 2018140094 A1 | 8/2018 |
| WO | 2018140095 A2 | 8/2018 |
| WO | 2018140096 A1 | 8/2018 |

OTHER PUBLICATIONS

"Archive History for NCT02844179 (+)—Alpha-Dihydrotetrabenazine Phase I" U.S. National Library of Medicine, https://clinicaltrials.gov/ct2/history/NCT02844179?V_1=View#StudyPageTop (2016).

Kilbourn, "Rat pancreas uptake of [11C]dihydrotetrabenazine stereoisomers" Nucl. Med. Biol. (2010), 37(8), pp. 869-871.

Boldt et al., "Synthesis of (+)- and (−)Tetrabenazine from the Resolution of [alpha]-Dihydrotetrabenazine", Synth. Commun., (2009), 39(20), pp. 3574-3585.

Yao, et al., "Preparation and Evaluation of Tetrabenazine Enantiomers and All Eight Stereoisomers of Dihydrotetrabenazine as VMAT2 Inhibitors", Eur. J. Med. Chem., 46, pp. 1841-1848, (2011).

Kilbourn, et al., "Binding of α-dihydrotetrabenazine to the Vesicular Monoamine Transporter is Stereospecific", Eur. J. Pharmacol., 278(3), pp. 249-252, (1995).

Bhatnagar, et al., "Pharmacokinetics of Dihydrotetrabenazine After Intravenous and Peroral Administration to Rats", Pharm Pharmacol Lett, 2(3), pp. 89-91, (1992).

Mehvar, et al., "Pharmacokinetics of Tetrabenazine and its Major Metabolite in Man and Rat", Drug Metab. Dispos., 15(2), pp. 250-255, (1987).

Roberts, et al., "The Pharmacokinetics of Tetrabenazine and its Hydroxy Metabolite in Patients Treated for Involuntary Movement Disorders", Eur. J. Clin. Pharmacol., 29, pp. 703-708., (1986).

Kilbourn, et al., "Absolute Configuration of (+)-α-Dihydrotetrabenazine, an Active Metabolite of Tetrabenazine", Chirality, 9, pp. 59-62, (1997).

Brossi, et al., "Syntheseversuche in der Emetin-Reihe, 3. Mittelung", Helv. Chim Acta., vol. XLI, No. 193, pp. 1793-1806, (1958) (and English Translation).

Schwartz, et al, "Metabolic Studies of Tetrabenazine, a Psychotropic Drug in Animals and Man", Biochem. Pharmacol., 15, pp. 645-655, (1956).

(Continued)

*Primary Examiner* — Rei Tsang Shiao
(74) *Attorney, Agent, or Firm* — Heslin Rothenberg Farley & Mesiti P.C.

(57) ABSTRACT

This invention relates to the use of combinations of stereoisomers of dihydrotetrabenazine for the treatment of movement disorders, such as Tourette's syndrome.

12 Claims, 6 Drawing Sheets

(56) References Cited

OTHER PUBLICATIONS

Scherman, et al., "Hydrophobicity of the Tetrabenazine-Binding Site of the Chromaffin Granule Monoamine Transporter", Mol. Pharmacol., 33, pp. 72-77, (1987).

Mehvar, et al., "Concentration-Effect Relationships of Tetrabenazine and Dihydrotetrabenazine in the Rat", J. Pharm. Sci., 76(6), pp. 461-465, (1987).

Kilbourn, et al., "PET Radioligands for Vesicular Neurotransmitter Transporters", Med. Chem. Res., 5, pp. 113-126, (1994).

Kilbourn, et al., "In Vivo Measures of Dopaminergic Radioligands in the Rat Brain: Equilibrium Infusion Studies", Synapse, 43, pp. 188-194, (2002).

Müller, "Valbenazine Granted Breakthrough Drug Status for Treating Tardive Dyskinesia", Expert Opin. Investig. Drugs, 24(6), pp. 737-742, (2015).

Hauser, et al., "KINECT 3: A Randomised, Double-Blind Placebo-Controlled Phase 3 Trial of Valbenazine (NBI-98854) for Tardive Dyskinesia (PL02.003)", Neurology, (2016), 86(16 Supplement). Abstract.

Hauser, et al., "KINECT 3: A Phase 3 Randomised, Double-Blind, Placebo-Controlled Trial of Valbenazine for Tardive Dyskinesia", Am. J. Psychiatry, 174(5), pp. 476-484, (2017).

Ashcroft, et al., "A Comparison of Tetrabenazine and Chlorpromazine in Chronic Schizophrenia", Br. J. Psychiatry, 107(447), pp. 287-293, (1961).

Chen, et al. "Tetrabenazine for the Treatment of Hyperkinetic Movement Disorders: A Review of the Literature", Clin. Ther., 34(7), pp. 1487-1504, (2012).

Shen, et al., "Safety and Efficacy of Tetrabenazine and Use of Concomitant Medications During Long-Term, Open-Label Treatment of Chorea Associated with Huntington's and Other Diseases", Tremor Other Hyperkinet Mov, 3, pp. 1-13., (2013).

Skor, et al., "Differences in Dihydrotetrabenazine Isomer Concentrations Following Administration of Tetrabenazine and Valbenazine", Drugs R&D, 17(3), pp. 449-459, (2017).

Duffield, et al., "Pharmaceutical Compositions", U.S. Appl. No. 15/939,826, filed Mar. 29, 2018, pp. 1-74.

Duffield, et al., "Pharmaceutical Compositions", U.S. Appl. No. 15/939,828, filed Mar. 29, 2018, pp. 1-48.

Duffield, et al., "Pharmaceutical Compositions", U.S. Appl. No. 15/939,831, filed Mar. 29, 2018, pp. 1-42.

Duffield, et al., "Pharmaceutical Compositions", U.S. Appl. No. 15/939,822, filed Mar. 29, 2018, pp. 1-71.

Walkup, J.T., "A Guide to Tourette Syndrome Medications", https://depts.washington.edu/dbpeds/A%20Guide%20to%20TS%20Medications_M-313.pdf, pp. 1-14 (2008).

* cited by examiner

COMBINATIONS OF ISOMERS OF DIHYDROTETRABENAZINE

CROSS REFERENCE TO RELATED APPLICATIONS

This application claims priority to U.S. Provisional Application No. 62/515,940, filed on Jun. 6, 2017, and to Great Britain Application No. 1705306.7, filed on Apr. 1, 2017. The entire contents of each of the prior applications are hereby incorporated herein by reference.

This invention relates to the use of combinations of stereoisomers of dihydrotetrabenazine for the treatment of movement disorders, such as Tourette's syndrome.

BACKGROUND OF THE INVENTION

Movement disorders can generally be classified into two categories: hyperkinetic movement disorders and hypokinetic movement disorders. Hyperkinetic movement disorders are caused by an increase in muscular activity and can cause abnormal and/or excessive movements, including tremors, dystonia, chorea, tics, myoclonus and stereotypies.

Hyperkinetic movement disorders often are often psychological in nature and arise through improper regulation of amine neurotransmitters in the basal ganglia.

A particular hyperkinetic movement disorder is Tourette's syndrome, which is an inherited neurological condition characterised by multiple physical and vocal tics. The tics are usually repetitive, but random, physical movements or vocal noises. The vocal tics can be of various forms and include repeating one's own words, the words of others or other sounds. Onset usually occurs in children and continues through to adolescence and adulthood.

While the tics associated with Tourette's syndrome are temporarily suppressible, those affected can usually only suppress their tics for limited time periods. There is yet to be an effective treatment to cover all types of tics in all patients, but certain medicaments for tic suppression have been developed.

It is known that dopamine receptor antagonists display an ability to suppress tics in Tourette's syndrome patients and a number dopamine receptor antagonists are currently used in the suppression of Tourette's tics, such as fluphenazine, haloperidol and pimozide.

Type 2 vesicular monoamine transporter (VMAT2) is a membrane protein responsible for the transportation of monoamine neurotransmitters, such as dopamine, serotonin and histamine, from cellular cytosol into synaptic vesicles. Inhibition of this protein hinders presynaptic neurons from releasing dopamine, resulting in a depletion of dopamine levels in the brain.

VMAT2 inhibitors can be used to treat the symptoms of Tourette's syndrome.

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders such as Huntington's disease, hemiballismus, senile chorea, tic, tardive dyskinesia and Tourette's syndrome, see for example Jankovic et al., *Am. J. Psychiatry.* (1999) August; 156(8):1279-81 and Jankovic et al., *Neurology* (1997) February; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks post-synaptic dopamine receptors.

The central effects of tetrabenazine closely resemble those of reserpine, but it differs from reserpine in that it lacks activity at the VMAT1 transporter. The lack of activity at the VMAT1 transporter means that tetrabenazine has less peripheral activity than reserpine and consequently does not produce VMAT1-related side effects such as hypotension.

Tetrabenazine is an effective and safe drug for the treatment of a variety of hyperkinetic movement disorders and, in contrast to typical neuroleptics, has not been demonstrated to cause tardive dyskinesia. Nevertheless, tetrabenazine does exhibit a number of dose-related side effects including causing depression, parkinsonism, drowsiness, nervousness or anxiety, insomnia and, in rare cases, neuroleptic malignant syndrome, see for example the introductory section of WO2016/127133 (Neurocrine Biosciences).

The chemical structure of tetrabenazine is as shown below.

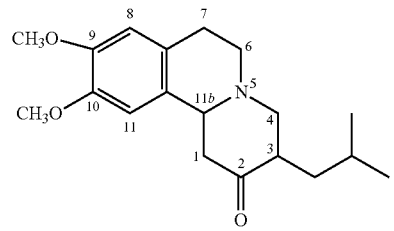

Structure of tetrabenazine

The compound has chiral centres at the 3 and 11b carbon atoms and hence can, theoretically, exist in a total of four isomeric forms, as shown below.

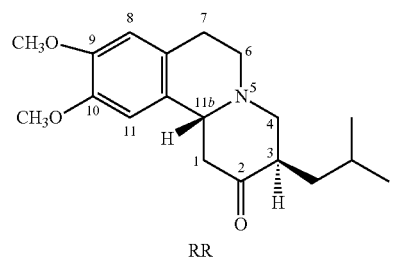

RR

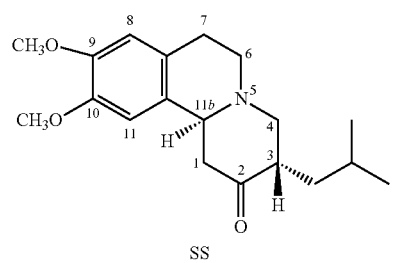

SS

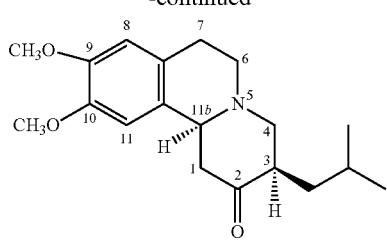

RS

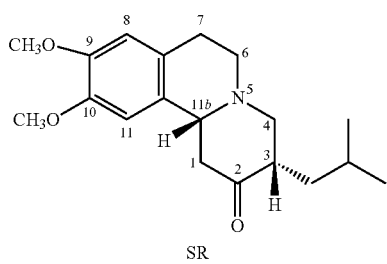

SR

Possible of tetrabenazine isomers

The stereochemistry of each isomer shown above is defined using the "R and S" nomenclature developed by Cahn, Ingold and Prelog, see *Advanced Organic Chemistry* by Jerry March, 4$^{th}$ Edition, John Wiley & Sons, New York, 1992, pages 109-114. Here and elsewhere in this patent application, the designations "R" or "S" are given in the order of the position numbers of the carbon atoms. Thus, for example, RS is a shorthand notation for 3R,11bS. Similarly, when three chiral centres are present, as in the dihydrotetrabenazines described below, the designations "R" or "S" are listed in the order of the carbon atoms 2, 3 and 11b. Thus, the 2R,3S,11bS isomer is referred to in short hand form as RSS and so on.

Commercially available tetrabenazine is a racemic mixture of the RR and SS isomers and the RR and SS isomers are generally considered to be the most thermodynamically stable isomers.

Tetrabenazine has somewhat poor and variable bioavailability. It is extensively metabolised by first-pass metabolism, and little or no unchanged tetrabenazine is typically detected in the urine. It is known that at least some of the metabolites of tetrabenazine are dihydrotetrabenazines formed by reduction of the 2-keto group in tetrabenazine.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

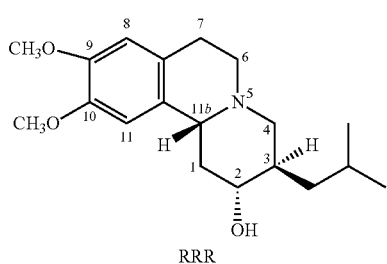

RRR

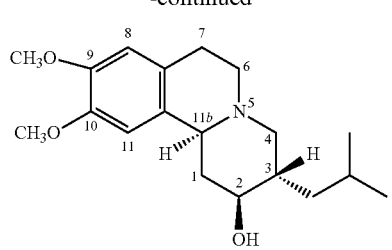

SSS

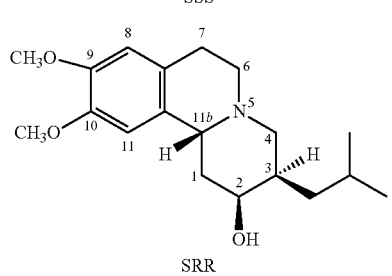

SRR

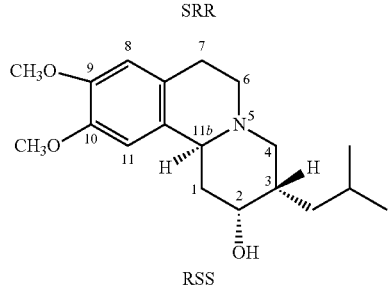

RSS

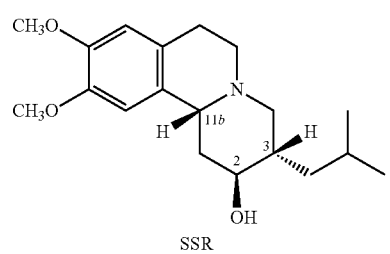

SSR

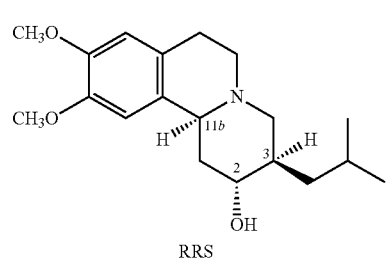

RRS

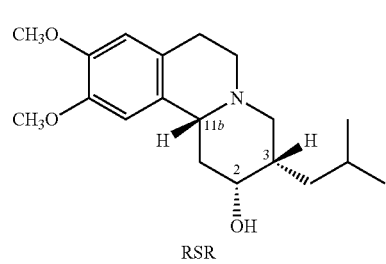

RSR

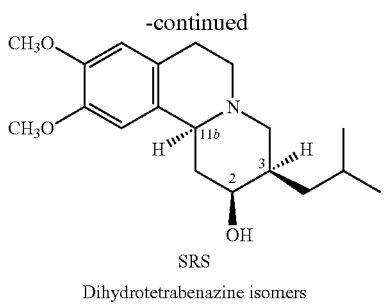

SRS

Dihydrotetrabenazine isomers

The synthesis and characterisation of all eight dihydrotetrabenazine isomers is described by Sun et al. (*Eur. J. Med. Chem.* (2011), 1841-1848).

Of the eight dihydrotetrabenazine isomers, four isomers are derived from the more stable RR and SS isomers of the parent tetrabenazine, namely the RRR, SSS, SRR and RSS isomers.

The RRR and SSS isomers are commonly referred to as "alpha (α)" dihydrotetrabenazines and can be referred to individually as (+)-α-dihydrotetrabenazine and (−)-α-dihydrotetrabenazine respectively. The alpha isomers are characterised by a trans relative orientation of the hydroxyl and 2-methylpropyl substituents at the 2- and 3-positions—see for example, Kilbourn et al., *Chirality*, 9:59-62 (1997) and Brossi et al., *Helv. Chim. Acta.*, vol. XLI, No. 193, pp 1793-1806 (1958).

The SRR and RSS isomers are commonly referred to as "beta (β)" isomers and can be referred to individually as (+)-β-dihydrotetrabenazine and (−)-β-dihydrotetrabenazine respectively. The beta isomers are characterised by a cis relative orientation of the hydroxyl and 2-methylpropyl substituents at the 2- and 3-positions.

Although dihydrotetrabenazine is believed to be primarily responsible for the activity of the drug, there have been no studies published to date that contain evidence demonstrating which of the various stereoisomers of dihydrotetrabenazine is responsible for its biological activity. More specifically, there have been no published studies demonstrating which of the stereoisomers is responsible for the ability of tetrabenazine to treat movement disorders such as Tourette's syndrome.

Schwartz et al. (*Biochem. Pharmacol.* (1966), 15: 645-655) describes metabolic studies of tetrabenazine carried out in rabbits, dogs and humans. Schwartz et al. identified nine metabolites, five of which were unconjugated and the other four of which were conjugated with glucuronic acid. The five unconjugated metabolites were the alpha- and beta-dihydrotetrabenazines, their two oxidised analogues in which a hydroxyl group has been introduced into the 2-methylpropyl side chain, and oxidised tetrabenazine in which a hydroxyl group has been introduced into the 2-methylpropyl side chain. The four conjugated metabolites were all compounds in which the 9-methoxy group had been demethylated to give a 9-hydroxy compound. The chirality of the various metabolites was not studied and, in particular, there was no disclosure of the chirality of the individual α- and β-isomers. Scherman et al., (*Mol. Pharmacol.* (1987), 33, 72-77 describes the stereospecificity of VMAT2 binding between racemic α- and β-isomers. They reported that α-dihydrotetrabenazine had a 3- to 4-fold higher affinity for the Chromaffin Granule Monoamine Transporter than the β-isomer, when studied in vitro. However, Scherman et al. does not disclose the resolution or testing of the individual enantiomers of the α- and β-dihydrotetrabenazines.

Mehvar et al. (*J. Pharm. Sci.* (1987), 76(6), 461-465) reported a study of the concentrations of tetrabenazine and dihydrotetrabenazine in the brains of rats following administration of either tetrabenazine or dihydrotetrabenazine. The study showed that despite its greater polarity, dihydrotetrabenazine was able to cross the blood-brain barrier. However, the stereochemistry of the dihydrotetrabenazine was not disclosed.

Mehvar et al. (*Drug Metabolism and Disposition* (1987), 15:2, 250-255) describes studies of the pharmacokinetics of tetrabenazine and dihydrotetrabenazine following administration of tetrabenazine to four patients affected by tardive dyskinesia. Oral administration of tetrabenazine resulted in low plasma concentrations of tetrabenazine but relatively high concentrations of dihydrotetrabenazine. However, the stereochemistry of the dihydrotetrabenazine formed in vivo was not reported.

Roberts et al. (*Eur. J. Clin. Pharmacol.* (1986), 29: 703-708) describes the pharmacokinetics of tetrabenazine and its hydroxy-metabolite in patients treated for involuntary movement disorders. Roberts et al. reported that tetrabenazine was extensively metabolised after oral administration resulting in very low plasma concentrations of tetrabenazine but much higher concentrations of a hydroxy-metabolite. Although they did not describe the identity of the hydroxy-metabolites, they suggested that the high plasma concentrations of the hydroxy-metabolites may be therapeutically important (since the metabolites were known to be pharmacologically active) and that, in view of the disclosure in Schwartz et al. (idem), the combination of cis and trans isomers (i.e. beta and alpha isomers) could be more therapeutically important than the parent drug.

Michael Kilbourn and collaborators at the University of Michigan Medical School have published a number of studies relating to the various isomers of dihydrotetrabenazines. In *Med. Chem. Res.* (1994), 5:113-126, Kilbourn et al. describe the use (+/−)-α-[11C]-dihydrotetrabenazine as in vivo imaging agents for VMAT2 binding studies.

In *Eur. J. Pharmacol* (1995) 278, 249-252, Kilbourn et al. reported competition binding studies using [3H]-tetrabenazine to study the in vitro binding affinity of (+)-, (−)-, and (+/−)-α-DHTBZ. The binding assays gave a Ki value of 0.97 nM for (+)-α-dihydrotetrabenazine and 2.2 µM for (−)-α-dihydrotetrabenazine, thereby showing that the (+) alpha isomer has much greater binding affinity for the VMAT2 receptor than the (−) alpha isomer. However, no studies were reported, or conclusions drawn, as to the usefulness of either isomer in the treatment of movement disorders such as Tourette's syndrome.

In *Chirality* (1997) 9:59-62, Kilbourn et al. described studies aimed at identifying the absolute configuration of (+)-α-dihydrotetrabenazine from which they concluded that it has the 2R, 3R, 11bR configuration shown above. They also referred to the Schwartz et al. and Mehvar et al. articles discussed above as indicating that the α- and β-dihydrotetrabenazines are likely to be the pharmacologically active agents in the human brain but they drew no explicit conclusions as to the precise stereochemical identities of the active metabolites of tetrabenazine.

In *Synapse* (2002), 43:188-194, Kilbourn et al. described the use of (+)-α-[$^{11}$C]-dihydrotetrabenazine as an agent used to measure specific in vivo binding of the VMAT receptor, in "infusion to equilibrium methods". They found that (−)-α-[$^{11}$C]-dihydrotetrabenazine produced a uniform brain distribution, consistent with the earlier observations that this enantiomer has a low VMAT affinity.

Sun et al. (idem) investigated the VMAT2 binding affinities of all eight dihydrotetrabenazine isomers. They found that all of the dextrorotatory enantiomers exhibited dramatically more potent VMAT2 binding activity than their corresponding laevorotatory enantiomers with the most active (+)-α-isomer being found to be the most active. However, Sun et al. did not carry out any investigations into the relative efficacies of the individual isomers in treating movement disorders such as Tourette's syndrome.

WO 2011/153157 (Auspex Pharmaceutical, Inc.) describes deuterated forms of dihydrotetrabenazine. Many deuterated forms of dihydrotetrabenazine are depicted but the application only provides sufficient information to allow a small number of the depicted compounds to be synthesised. Although racemic mixtures of $d_6$-α-dihydrotetrabenazine and $d_6$-β-dihydrotetrabenazine are disclosed, these mixtures were not resolved and the properties of the individual (+) and (−) isomers were not studied. Similarly, WO 2014/047167 (Auspex Pharmaceutical, Inc.) describes a number of deuterated forms of tetrabenazine and its derivatives. Again, the individual (+) and (−) isomers of deuterated forms of α- and β-dihydrotetrabenazine were not separated or studied.

WO 2006/053067 (Prestwick) described the use of combinations of amantadine and tetrabenazine for treating hyperkinetic movement disorders. Although the document is primarily concerned with using tetrabenazine, it is envisaged that amantadine can be administered with a "tetrabenazine compound" which may be tetrabenazine or dihydrotetrabenazine.

The Examples section of the patent application only discloses experimental protocols of how the combinations of amantadine and tetrabenazine could be administered. Based on the wording of the Examples section, it appears that the combinations had not been administered at the time the application was filed and the application contains no results demonstrating the efficacy of combinations of amantadine and tetrabenazine.

In addition, the Examples section only describes the use of tetrabenazine rather than any dihydrotetrabenazine isomers.

SUMMARY OF THE INVENTION

As discussed above, the studies carried out by Schwartz et al. (idem) demonstrated that both alpha and beta isomers of tetrabenazine are formed as metabolites of tetrabenazine. However, the precise stereochemical configurations of the alpha and beta isomers were not investigated.

Studies in human subjects carried out by the present applicants and described in Example 1 below have now confirmed the findings of Schwartz et al. that major metabolites of tetrabenazine are indeed alpha and beta dihydrotetrabenazines. However, contrary to what has previously been suggested, the main metabolites produced upon administration of tetrabenazine are the (−)-α-dihydrotetrabenazine isomer, which is essentially active as a VMAT2 binding agent, and the (+)-β-dihydrotetrabenazine isomer, which is significantly less active than the (+)-α-dihydrotetrabenazine isomer.

Thus, in a single dose study involving the administration of tetrabenazine to adult male humans, the $C_{max}$ figures for (+)-β-dihydrotetrabenazine and (−)-α-dihydrotetrabenazine respectively were 103 and 72.94 ng/ml whereas the $C_{max}$ figures for (−)-β-dihydrotetrabenazine and (+)-α-dihydrotetrabenazine respectively were 5.28 and 2.61 ng/ml. The area under the curve (AUC) figures for each of the (+)-β-dihydrotetrabenazine, (−)-α-dihydrotetrabenazine, (−)-β-dihydrotetrabenazine and (+)-α-dihydrotetrabenazine metabolites respectively were 375.78, 305.84, 16.28 and 7.98. A similar distribution of metabolites was found when multiple doses of tetrabenazine were administered.

On the basis of these findings, it is envisaged that combinations of (+)-β-dihydrotetrabenazine, having the formula (III),

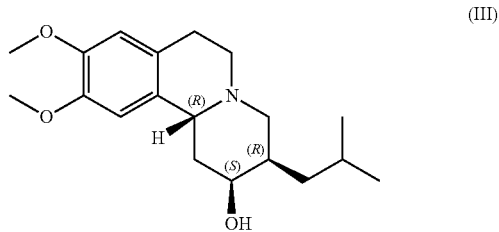

and (−)-α-dihydrotetrabenazine, having the formula (II),

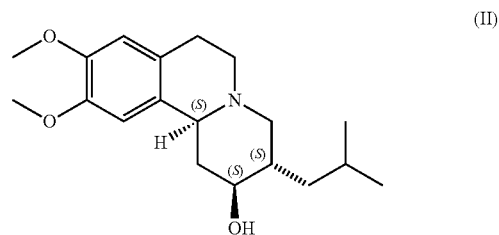

and/or (+)-α-dihydrotetrabenazine, having the formula (I),

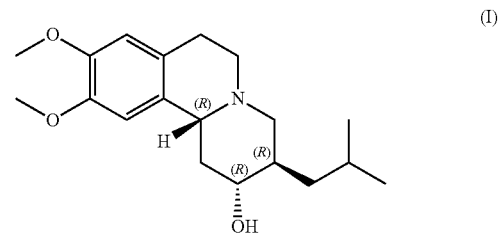

will be useful in the prophylaxis or treatment of inter alia the disease states and conditions for which tetrabenazine is currently used or proposed. Thus, by way of example, and without limitation, it is envisaged that these combinations of dihydrotetrabenazine isomers may be used for the treatment of hyperkinetic movement disorders such as Huntington's disease, hemiballismus, senile chorea, tic disorders, tardive dyskinesia, dystonia and, in particular, Tourette's syndrome.

Accordingly, in a first aspect, the invention provides a pharmaceutical combination comprising:

(a) (+)-β-dihydrotetrabenazine, or a pharmaceutically acceptable salt thereof; and one or both of:

(b) (−)-α-dihydrotetrabenazine, or a pharmaceutically acceptable salt thereof; and (c) (+)-α-dihydrotetrabenazine, or a pharmaceutically acceptable salt thereof.

In one embodiment, the invention provides a pharmaceutical combination comprising:

(a) (+)-β-dihydrotetrabenazine, or a pharmaceutically acceptable salt thereof; and (b) (−)-α-dihydrotetrabenazine, or a pharmaceutically acceptable salt thereof.

In another embodiment, the invention provides a pharmaceutical combination comprising:

(a) (+)-β-dihydrotetrabenazine, or a pharmaceutically acceptable salt thereof; and (c) (+)-α-dihydrotetrabenazine, or a pharmaceutically acceptable salt thereof.

In another embodiment, the invention provides a pharmaceutical combination comprising:

(a) (+)-β-dihydrotetrabenazine, or a pharmaceutically acceptable salt thereof;

(b) (−)-α-dihydrotetrabenazine, or a pharmaceutically acceptable salt thereof; and (c) (+)-α-dihydrotetrabenazine, or a pharmaceutically acceptable salt thereof.

The (+)-β-dihydrotetrabenazine, (−)-α-dihydrotetrabenazine and (+)-α-dihydrotetrabenazine may be referred to herein collectively as "the dihydrotetrabenazine isomers of the invention" or "isomers of dihydrotetrabenazine" or "the dihydrotetrabenazines", unless the context indicates otherwise. When describing types of pharmaceutical formulation, they may also be referred to collectively as the "active compounds".

The pharmaceutical combination may be substantially free of (−)-β-dihydrotetrabenazine. Accordingly, the invention also provides a pharmaceutical combination as described herein, wherein the unit dosage form is substantially free of (−)-β-dihydrotetrabenazine.

By "substantially free of (−)-β-dihydrotetrabenazine" is meant that the % weight of (−)-β-dihydrotetrabenazine present compared to the total weight of all isomers of dihydrotetrabenazine is less than 5%, preferably less than 3%, more preferably less than 2% and most preferably less than 1%.

The relative proportions of the (+)-β-dihydrotetrabenazine, (−)-α-dihydrotetrabenazine and (+)-α-dihydrotetrabenazine may be expressed in terms of parts by weight of the individual isomers. Thus, for example, the unit dosage forms may comprise from 35 to 75 parts by weight of (+)-β-dihydrotetrabenazine and from 25 to 55 parts by weight of an α-dihydrotetrabenazine (which may be either (+)-α-dihydrotetrabenazine or (−)-α-dihydrotetrabenazine or a mixture thereof). It will be appreciated that the proportions expressed above as parts by weight could instead be expressed in terms of molar ratios (as all of the isomers have the same molecular weight), in which case the relative proportions of the isomers could be expressed as a molar ratio of (+)-β-dihydrotetrabenazine:α-dihydrotetrabenazine (which may be either (+)-α-dihydrotetrabenazine or (−)-α-dihydrotetrabenazine or a mixture thereof) of 35-70:25-55.

In one embodiment, a pharmaceutical combination of the invention comprises:

(a) 40-65 parts by weight of (+)-β-dihydrotetrabenazine, or a pharmaceutically acceptable salt thereof; and (c) 40-65 parts by weight of (+)-α-dihydrotetrabenazine, or a pharmaceutically acceptable salt thereof.

For example, the pharmaceutical combination may comprise:

(a) 45-55 parts by weight of (+)-β-dihydrotetrabenazine, or a pharmaceutically acceptable salt thereof; and (c) 45-55 parts by weight of (+)-α-dihydrotetrabenazine, or a pharmaceutically acceptable salt thereof.

In one particular embodiment, the pharmaceutical combination comprises (+)-β-dihydrotetrabenazine and (+)-α-dihydrotetrabenazine in approximately equimolar amounts.

In another embodiment, a pharmaceutical combination of the invention comprises:

(a) 45-65 parts by weight of (+)-β-dihydrotetrabenazine, or a pharmaceutically acceptable salt thereof;

(b) 30-50 parts by weight of (−)-α-dihydrotetrabenazine, or a pharmaceutically acceptable salt thereof; and optionally (c) 0.1-5 parts by weight of (+)-α-dihydrotetrabenazine, or a pharmaceutically acceptable salt thereof.

In another embodiment, a pharmaceutical combination of the invention comprises:

(a) 45-65 parts by weight of (+)-β-dihydrotetrabenazine, or a pharmaceutically acceptable salt thereof;

(b) 30-50 parts by weight of (−)-α-dihydrotetrabenazine, or a pharmaceutically acceptable salt thereof; and optionally (c) 0.1-3 parts by weight of (+)-α-dihydrotetrabenazine, or a pharmaceutically acceptable salt thereof.

In another embodiment, a pharmaceutical combination of the invention comprises:

(a) 45-65 parts by weight of (+)-β-dihydrotetrabenazine, or a pharmaceutically acceptable salt thereof;

(b) 30-50 parts by weight of (−)-α-dihydrotetrabenazine, or a pharmaceutically acceptable salt thereof; and optionally (c) 0.1-2 parts by weight of (+)-α-dihydrotetrabenazine, or a pharmaceutically acceptable salt thereof.

In a further embodiment, a pharmaceutical combination of the invention comprises:

(a) 45-65 parts by weight of (+)-β-dihydrotetrabenazine, or a pharmaceutically acceptable salt thereof;

(b) 30-50 parts by weight of (−)-α-dihydrotetrabenazine, or a pharmaceutically acceptable salt thereof; and optionally (c) 0.1-1.5 parts by weight of (+)-α-dihydrotetrabenazine, or a pharmaceutically acceptable salt thereof.

By pharmaceutical combination is meant a combination of the three dihydrotetrabenazines (a) and (b) and/or (c) in a form that is suitable for administration to a subject, typically a human or other animal subject. The term therefore excludes crude reaction mixtures, partially purified reaction products, whole blood samples or blood fraction samples such as plasma or other biological samples such as urine samples containing the combinations. It also excludes simple solutions of the combinations in non-pharmaceutically acceptable solvents (e.g. chloroform, dichloromethane) that are not normally used in pharmacy.

The pharmaceutical combinations may be in the form of mixtures of the pure compounds or the combinations may comprise one or more pharmaceutically acceptable excipients.

Typically, the pharmaceutical combinations comprise a pharmaceutically acceptable excipient and are formulated as unit dosage forms containing defined amounts of the dihydrotetrabenazines (a), (b) and/or (c).

In the pharmaceutical combinations of the invention, one or more of the three dihydrotetrabenazines (a), (b) and (c) may be formulated separately but used in combination. More typically, however, the three dihydrotetrabenazines (a), (b) and (c) are formulated together in a pharmaceutical composition, and in particular a unit dosage form.

In a unit dosage form of the invention containing a combination as defined herein, the sum of the amounts of the three isomers (+)-β-dihydrotetrabenazine, (−)-α-dihydrotetrabenazine and (+)-α-dihydrotetrabenazine (the "total amount") may be selected so that it does not exceed 100 mg.

In particular embodiments:
the total amount of the three isomers does not exceed 75 mg; or
the total amount of the three isomers does not exceed 50 mg; or
the total amount of the three isomers does not exceed 40 mg; or
the total amount of the three isomers does not exceed 30 mg; or
the total amount of the three isomers does not exceed 20 mg.

The unit dosage form can be one which is administered orally, for example a capsule or tablet.

The pharmaceutical combinations as defined herein are provided for use in medicine.

More particularly, the pharmaceutical combinations (and unit dosage forms) defined and described above are provided for use in the treatment of a hyperkinetic movement disorder such as Huntington's disease, hemiballismus, senile chorea, tic disorders, tardive dyskinesia, dystonia and Tourette's syndrome.

More particularly, the pharmaceutical combinations (and unit dosage forms) described above are for use in the treatment of a hyperkinetic movement disorder selected from tic disorders, tardive dyskinesia and Tourette's syndrome.

In one particular embodiment, the pharmaceutical combinations (and unit dosage forms) described above are for use in the treatment of tardive dyskinesia.

In another particular embodiment, the pharmaceutical combinations (and unit dosage forms) described above are for use in the treatment of Tourette's syndrome.

In further aspects, the invention provides:
A pharmaceutical combination as defined herein for use in the treatment of a hyperkinetic movement disorder.
A method of treatment of a hyperkinetic movement disorder in a subject in need thereof (e.g. a mammalian subject such as a human), which method comprises administering to the subject a therapeutically effective amount of a pharmaceutical combination as defined herein.
The use of a pharmaceutical combination as defined herein for the manufacture of a medicament for the treatment of a hyperkinetic movement disorder.
A unit dosage form for use, a pharmaceutical combination for use, a method or a use as described herein wherein the hyperkinetic movement disorder is selected from Huntington's disease, hemiballismus, senile chorea, tic disorders, tardive dyskinesia, dystonia and Tourette's syndrome.
A unit dosage form for use, a pharmaceutical combination for use, a method or a use as described herein wherein the hyperkinetic movement disorder is Tourette's syndrome.

In each case, the combination of (+)-β-dihydrotetrabenazine, (−)-α-dihydrotetrabenazine; and optionally (+)-α-dihydrotetrabenazine is typically administered once per day.

Complete blocking of VMAT2 is considered undesirable as this can lead to unwanted side effects, such as Parkinsonism. The present invention provides plasma levels of dihydrotetrabenazines that are sufficient to give effective treatment of movement disorders but do not block VMAT2 to an extent that causes Parkinsonism and similar side effects. The levels of VMAT2 blocking can be determined by competitive binding studies using Positron Emission Tomography (PET). By co-administering a radioactive ligand with the compound of interest at various concentrations, the proportion of binding sites occupied can be determined (see for example, Matthews et al., "Positron emission tomography molecular imaging for drug development", *Br. J. Clin. Pharmacol.,* 73:2, 175-186).

Accordingly, the invention also provides:
A unit dosage form for use, a pharmaceutical combination for use, a method or a use as described herein, wherein the treatment comprises administering to the subject an amount of the unit dosage form or combination sufficient to cause a blocking level of greater than 20% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of greater than 30% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of greater than 40% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of less than 90% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of less than 85% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of less than 80% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of less than 75% of VMAT2 proteins in the subject.
A unit dosage form for use, a pharmaceutical combination for use, a method or a use as described herein, wherein the treatment comprises administering to the subject an amount of the unit dosage form or combination sufficient to cause a blocking level of less than 70% of VMAT2 proteins in the subject.
A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 20% to 90% (e.g. between 20% and 90%).
A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 30% to 80% (e.g. between 30% and 80%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 30% to 75% (e.g. between 30% and 75%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 30% to 70% (e.g. between 30% and 70%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 30% to 65% (e.g. between 30% and 65%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 30% to 60% (e.g. between 30% and 60%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 40% to 80% (e.g. between 40% and 80%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 40% to 75% (e.g. between 40% and 75%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 40% to 70% (e.g. between 40% and 70%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 40% to 65% (e.g. between 40% and 65%).

A unit dosage form for use, a pharmaceutical combination for use, a method or a use as described herein, wherein the treatment comprises administering to the subject an amount of the unit dosage form or combination sufficient to cause a level of blocking of VMAT2 proteins in the subject of from 40% to 60% (e.g. between 40% and 60%).

In each of the foregoing aspects and embodiments of the invention relating to combinations, typically the combinations of dihydrotetrabenazines (a) and (b) and/or (c) are not administered with a therapeutically effective amount of amantadine. More particularly, the combinations, are not administered with any amount of amantadine.

For example, with reference to pharmaceutical unit dosage forms, typically the unit dosage form does not comprise a therapeutically effective amount of amantadine and, more particularly, the pharmaceutical unit dosage form does not comprise any amount of amantadine.

Furthermore, in each of the foregoing aspects and embodiments of the invention relating to combinations of dihydrotetrabenazines (a) and (b) and/or (c), the pharmaceutical unit dosage form may be other than an extended release or delayed release dosage form.

Thus, for example, the combinations of dihydrotetrabenazines (a) and (b) and/or (c) may be administered as an immediate release unit dosage form.

Free Bases and Salts

The dihydrotetrabenazines (i.e. the (+)-β-dihydrotetrabenazine, (−)-α-dihydrotetrabenazine and (+)-α-dihydrotetrabenazine) may each be presented in the form of the free bases or as salts. All references herein to dihydrotetrabenazine isomers include both free bases and salts thereof unless the context indicates otherwise.

In one embodiment, one or more (e.g. all) of the dihydrotetrabenazines are in free base form.

In another embodiment, one or more (e.g. all) of the dihydrotetrabenazines are in the form of salts.

The salts are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two; generally, nonaqueous media such as ether, ethyl acetate, ethanol, isopropanol, or acetonitrile are used.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed" in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Isotopes

The dihydrotetrabenazine isomers (i.e. the (+)-β-dihydrotetrabenazine, (−)-α-dihydrotetrabenazine and (+)-α-dihydrotetrabenazine isomers) may each contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{11}C$, $^{12}C$, $^{13}C$ and $^{14}C$ and $^{16}O$ and $^{18}O$.

Typically, the dihydrotetrabenazine isomers of the invention do not contain non-naturally occurring isotopes (such as $^{11}C$ or $^3H$).

In one embodiment, the percentage of the total hydrogen atoms in the dihydrotetrabenazine isomers used in the invention that are deuterium atoms is less than 2%, preferably less than 1%, more preferably less than 0.1% and even more preferably less than 0.05%.

In an analogous manner, a reference to a particular functional group also includes within its scope isotopic variations, unless the context indicates otherwise.

The isotopes may be radioactive or non-radioactive. In one embodiment of the invention, the dihydrotetrabenazine isomers for use in the invention contain no radioactive isotopes. Such compounds are preferred for therapeutic use. In another embodiment, however, the dihydrotetrabenazine isomers may contain one or more radioisotopes. Compounds containing such radioisotopes may be useful in a diagnostic context.

Solvates

The isomers of dihydrotetrabenazine may form solvates. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as hydrates, the isomers of dihydrotetrabenazine may be anhydrous. Therefore, in another embodiment, one of more of the dihydrotetrabenazine isomers are in an anhydrous form. The unit dosage forms and combinations of the invention may contain dihydrotetrabenazine isomers which are all in anhydrous form, or are all in hydrate form, or contain mixtures or hydrated and anhydrous isomers.

Methods for the Preparation of the Dihydrotetrabenazine Isomers (+)-α-Dihydrotetrabenazine and (−)-α-dihydrotetrabenazine can be prepared from tetrabenazine according to the synthetic route shown in Scheme 1.

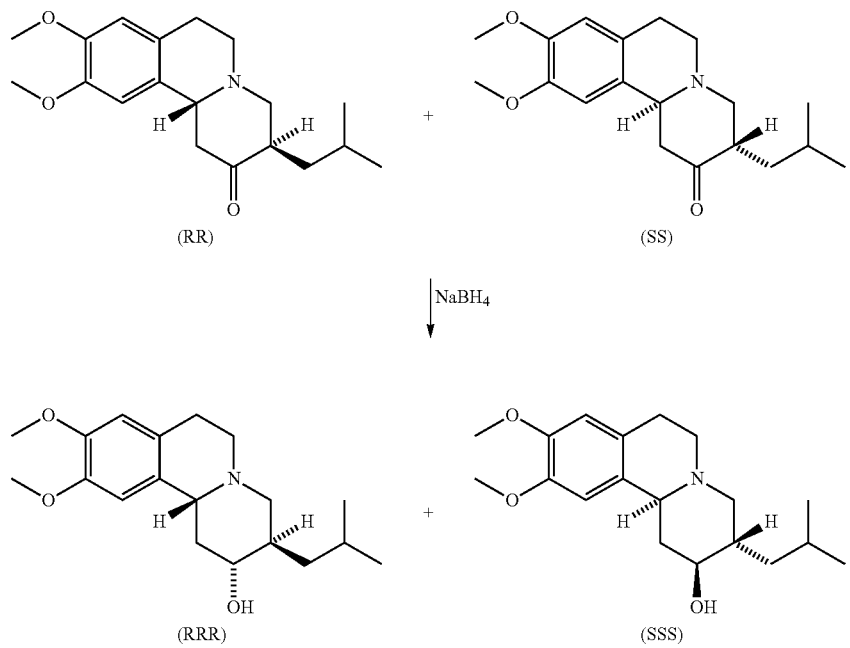

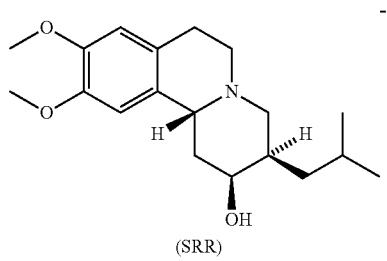
(SRR)

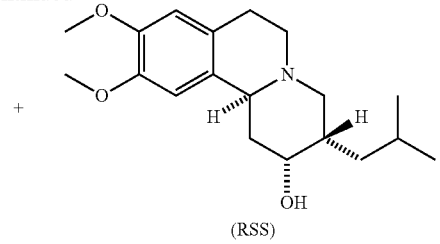
(RSS)

(I) Resolution of isomers (II)

Racemic tetrabenazine (3-isobutyl-9,10-dimethyoxy-1,3,4,6,7,11b-hexahydro-2H-pyrido[2,1,a]isoquinolin-2-one) containing the RR and SS isomers of tetrabenazine is reduced with sodium borohydride to afford a mixture of four dihydrotetrabenazine isomers of which a racemic mixture of the α-dihydrotetrabenazine (RRR and SSS isomers) constitutes the major product and a racemic mixture of the β-dihydrotetrabenazines (the SRR and RSS isomers) constitutes a minor product. The β-dihydrotetrabenazines can be removed during an initial purification procedure, for example by chromatography or recrystallization and then the racemic α-dihydrotetrabenazines resolved.

By recrystallization of the racemic mixture with di-p-toluoyl-L-tartaric acid or (R)-(−)-camphorsulfonic acid, or by chiral chromatography, the (+)-α-dihydrotetrabenazine isomer (I) ((2R,3R,11bR)-3-isobutyl-9,10-dimethoxy-1,3,4,6,7,11b-hexahydro-2H-pyrido[2,1,a]isoquinolin-2-ol) can be obtained. The stereochemical configuration of (+)-α-dihydrotetrabenazine can be determined, for example by forming a salt such as the mesylate salt in crystalline form and the structure identified by X-ray crystallography.

By recrystallization of the racemic mixture with di-p-toluoyl-R-tartaric acid or (L)-(+)-camphorsulfonic acid or by chiral chromatography, the (−)-α-dihydrotetrabenazine isomer (II) ((2S,3S,11bS)-3-isobutyl-9,10-dimethoxy-1,3,4,6,7,11b-hexahydro-2H-pyrido[2,1,a]isoquinolin-2-ol) can be obtained. The stereochemical configuration of (−)-α-dihydrotetrabenazine can be determined, for example, by forming a salt such as the mesylate salt in crystalline form and the structure identified by X-ray crystallography.

(+)-β-Dihydrotetrabenazine (compound of formula (III)) can be prepared from tetrabenazine according to the synthetic route shown in Scheme 2.

Scheme 2

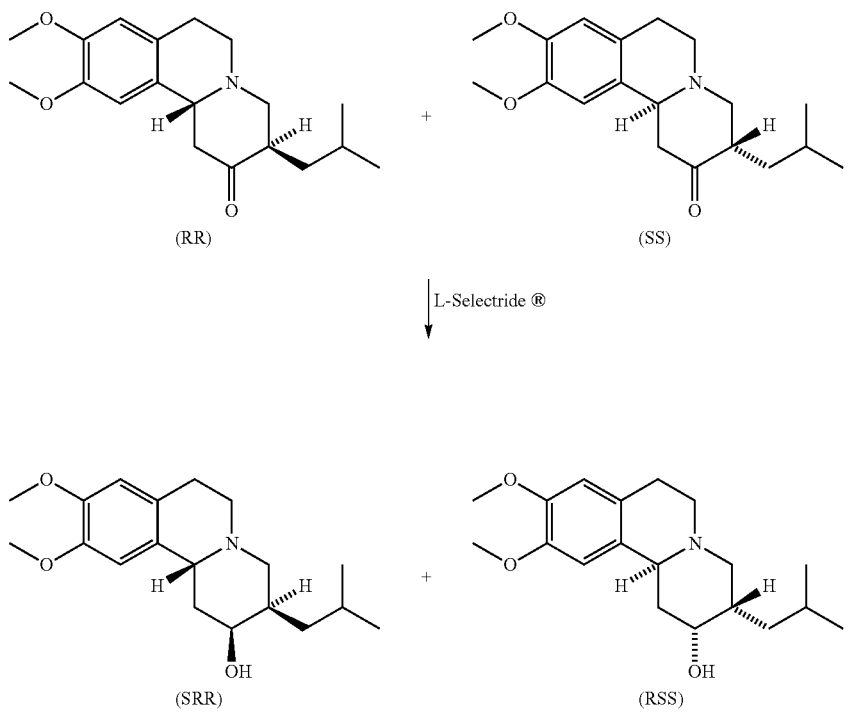

-continued

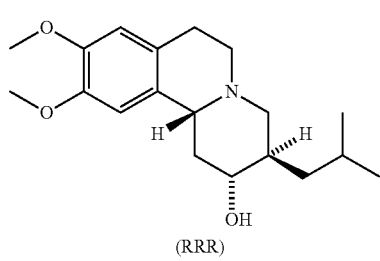
(RRR)

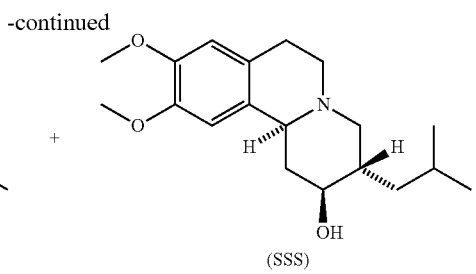
(SSS)

↓ Resolution of isomers (III)

Racemic tetrabenazine (3-isobutyl-9,10-dimethyoxy-1,3,4,6,7,11b-hexahydro-2H-pyrido[2,1,a]isoquinolin-2-one) containing the RR and SS isomers of tetrabenazine is reduced with sodium borohydride to afford a mixture of four dihydrotetrabenazine isomers of which a racemic mixture of the β-dihydrotetrabenazines (SRR and RSS isomers) constitutes the major product and a racemic mixture of the α-dihydrotetrabenazines (the RRR and SSS isomers) constitutes a minor product. The α-dihydrotetrabenazines can be removed during an initial purification procedure, for example by chromatography or recrystallization and then the racemic β-dihydrotetrabenazines resolved (e.g. by recrystallisation with di-p-toluoyl-L-tartaric acid or (R)-(−)-camphorsulfonic acid or by chiral chromatography), to afford (+)-β-dihydrotetrabenazine (III) ((2S,3R,11bR)-3-isobutyl-9,10-dimethoxy-1,3,4,6,7,11b-hexahydro-2H-pyrido[2,1,a]isoquinolin-2-ol). The stereochemical configuration of (+)-β-dihydrotetrabenazine can be determined, so example by forming a salt such as the mesylate salt in crystalline form and the structure identified by X-ray crystallography.

(+)-α-Dihydrotetrabenazine, (−)-α-dihydrotetrabenazine and (+)-β-dihydrotetrabenazine can also be prepared according to Yao et al., "Preparation and evaluation of tetrabenazine enantiomers and all eight stereoisomers of dihydrotetrabenazine as VMAT2 inhibitors", Eur. J. Med. Chem., (2011), 46, pp. 1841-1848.

Once prepared and purified, the (+)-β-dihydrotetrabenazine, (−)-α-dihydrotetrabenazine and, where present the (+)-α-dihydrotetrabenazine, or their respective salts, can be mixed in the required proportions.

Pharmaceutical Formulations

The unit dosage forms of the invention can be in any form suitable for oral, parenteral, topical, intranasal, intrabronchial, ophthalmic, otic, rectal, intra-vaginal, or transdermal administration. Where the unit dosage forms are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches. In one embodiment, the dosage form is a tablet. In another embodiment, the dosage form is a capsule.

Pharmaceutical unit dosage forms containing the dihydrotetrabenazine compound of the invention can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Unit dosage forms for topical use include ointments, creams, sprays, patches, gels, liquid drops and inserts (for example intraocular inserts). Such unit dosage forms can be formulated in accordance with known methods.

Unit dosage forms for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Unit dosage forms for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

Particular unit dosage forms of the invention are compositions selected from:
  Sublingual compositions;
  Intranasal compositions;
  Pellets or tablets formulated to provide release kinetics corresponding to zero order release of the active compound;
  Pellets or tablets formulated to provide first fast release followed by constant rate release (zero order) of the active compound;
  Pellets or tablets formulated to provide a mixture of first order and zero order release of the active compound; and
  Pellets or tablets formulated to provide a combination of zero order and first order release of the active compound; and optionally a further order of release of the active compound selected from second, third and fourth orders of release and combinations thereof.

Pellets and tablets formulated to provide release kinetics of the types defined above can be prepared according to methods well known the skilled person; for example as described in Remington's Pharmaceutical Sciences (idem) and "Remington—The Science and Practice of Pharmacy, 21$^{st}$ edition, 2006, ISBN 0-7817-4673-6.

The (+)-β-dihydrotetrabenazine, (−)-α-dihydrotetrabenazine and (+)-α-dihydrotetrabenazine may each be formulated separately into a unit dosage form as described above and then used in combination. Alternatively, one or more of the three (for example all three) dihydrotetrabenazines may be formulated together.

Where two or more of the three dihydrotetrabenazines are formulated together, they can be mixed before being subjected to formulating methods. For example, they can be mixed and the resulting mixture admixed with one or more excipients and processed (e.g. compressed or filled into capsules) to form a solid pharmaceutical composition.

In a variation, two or more of the three dihydrotetrabenazines may be formulated separately as mini-tablets, pellets, microbeads, granules, or other divided pharmaceutical forms, and then combined, for example by filling into a capsule shell or by compression together with one or more compression aids and fillers to form a tablet.

In another variation, a unit dosage form containing two or more of the dihydrotetrabenazines can be presented as a multilayer tablet, wherein one or more layers contain one (or two) of the dihydrotetrabenazines and one or more other layers contain the other dihydrotetrabenazine.

The compounds of the invention will generally be presented in unit dosage form and, as such, will typically contain an amount of compound sufficient to provide a desired level of biological activity. Such amounts are set out above.

The active compound will be administered to a subject (patient) in need thereof (for example a human or animal patient) in an amount sufficient to achieve the desired therapeutic effect, as described above.

EXAMPLES

Example 1

Figure 1:
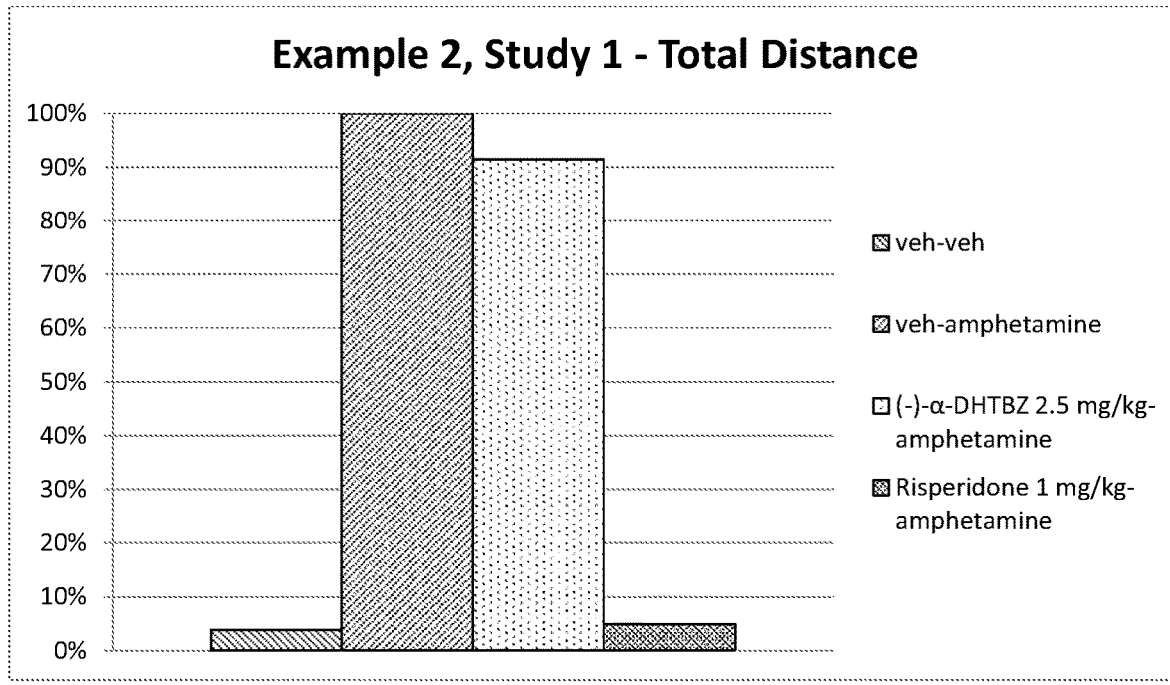
FIG. 1 shows the average total distance travelled by rats when treated with vehicle (with or without amphetamine induction) and (−)-α-dihydrotetrabenazine at a dose of 2.5 mg/kg and risperidone at a dose of 1 mg/kg in amphetamine-induced rats, as described in Example 2, Study 1 below.

An Investigation Into the Nature of the Dihydrotetrabenazine Metabolites Formed After Administration of Tetrabenazine to Human Subjects A pharmacokinetic study was carried out in healthy adult male volunteers under fasting conditions at a dose of single and multiple oral administration of 25 mg tablets once a day to ascertain the plasma levels of +/−α and +/−β dihydrotetrabenazine. The data are summarised below.

Table 1 summarises the pharmacokinetic data obtained following single-dose oral administration of tetrabenazine at a dose level of 25 mg (fasting, N=08).

TABLE 1

| Analyte | $T_{max}$ Mean (h) | $C_{max}$ (ng/mL) | AUC(0-t) (ng · h/mL) | AUC(0-inf.) (ng · h/mL) | $K_{el}$ NA | Half-life (Mean) (h) | Extrapolated AUC (%) |
|---|---|---|---|---|---|---|---|
| Tetrabenazine | 0.87 | 0.58 | 1.87 | 2.42 | 0.19 | 4.35 | 27.54 |
| (+) α-DHTBZ | 1.16 | 2.61 | 7.98 | 10.83 | 0.17 | 4.79 | 32.10 |
| (−) α-DHTBZ | 0.938 | 72.94 | 305.84 | 351.80 | 0.10 | 7.89 | 10.59 |
| (+) β-DHTBZ | 1.125 | 103.00 | 375.78 | 410.46 | 0.13 | 5.80 | 5.03 |
| (−) β-DHTBZ | 1.03 | 5.28 | 16.28 | 18.77 | 0.45 | 12.98 | 17.66 |

Table 2 summarises the pharmacokinetic data obtained following multiple-dose oral administration of tetrabenazine at a dose level of 25 mg (fasting, N=07).

TABLE 2

| Analyte | $T_{maxss}$ Mean (h) | $C_{maxss}$ (ng/mL) | $C_{minss}$ (ng/mL) | AUC(0-t) (ng · h/ mL) | $C_{tss}$ (ng/ mL) | $C_{avg}$ (ng · h/ mL) |
|---|---|---|---|---|---|---|
| Tetrabenazine | 96.89 | 0.73 | 0.01 | 2.79 | 0.10 | 0.12 |
| (+) α-DHTBZ | 97.18 | 3.31 | 0.00 | 13.74 | 0.44 | 0.57 |
| (−) α-DHTBZ | 96.96 | 98.34 | 5.61 | 474.17 | 6.10 | 19.76 |
| (+) β-DHTBZ | 97.11 | 144.76 | 5.45 | 598.76 | 5.54 | 24.95 |
| (−) β-DHTBZ | 97.11 | 7.78 | 0.16 | 25.17 | 0.57 | 1.05 |

The data presented in Tables 1 and 2 demonstrate that, in humans, the major metabolites are the (−)-α-dihydrotetrabenazine isomer, which is essentially active as a VMAT2 binding agent, and the (+)-β-dihydrotetrabenazine isomer, which is significantly less active than the (+)-α-dihydrotetrabenazine isomer. (−)-β-Dihydrotetrabenazine and (+)-α-dihydrotetrabenazine were shown to be minor metabolites The data suggest that (+)-α-dihydrotetrabenazine is not primarily responsible for the therapeutic properties of tetrabenazine. On the contrary, it appears that (+)-β-dihydrotetrabenazine may be primarily responsible for the VMAT2 blocking activities of tetrabenazine.

Example 2

Materials and Methods

Equipment

Open field arena, Med Associates Inc.

Plastic syringes 1 ml, Terumo. Ref: SS-01T1

Animal feeding needle 15 G, Instech Solomon, Cat: 72-4446

Sartorius Mechatronics Scale A22101, Sartorius Weighting Technology, Germany

Needle 27 G Terumo Myjector, 0.5 ml, Ref: 8300010463

Plastic syringes 3 ml, Soft-Ject, Ref: 8300005761

BD Microtainer K2EDTA tubes Ref: 365975

Matrix 0.75 ml, Alphanum Tubes, Thermo Scientific, Ref: 4274

Microplate Devices, Uniplate 24 wells, 10 ml, Ref: 734-1217

Thermo Electron Corp. Heraeus Fresco 17, refrigerated centrifuge

Test Animals

All animal experiments were carried out according to the National Institute of Health (NIH) guidelines for the care and use of laboratory animals, and approved by the National Animal Experiment Board, Finland. Male CD (Charles River Laboratories, Germany) at weight range of 200-250 g (165-200 g upon arrival) were used for the experiments. Animals were housed at a standard temperature (22±1° C.) and in a light-controlled environment (lights on from 7 am to 8 pm) with ad libitum access to food and water.

Methods

The locomotor activity of the rats was tested in an open field arena. The open field test was performed during the rat light cycle and under a normal lighting evenly distributed to the test chambers. The paths of the rats were recorded by activity monitor (Med. Associates Inc.).

Dosing the vehicle, amphetamine, (+)-α-DHTBZ, (−)-α-DHTBZ, (+)-β-DHTBZ, (−)-β-DHTBZ or risperidone was done prior to LMA test. The rats were placed in the centre of the arena, and the path was recorded for 30 minutes. After 30 minutes of testing, vehicle or amphetamine was dosed and the rat was placed in the centre of the arena, and the path was recorded for 60 minutes, the total testing time being 90 minutes.

Endpoint, Blood Samples and Tissue Processing

Within 10 minutes from the end of the test animals were euthanized by an overdose of $CO_2$. The terminal blood sample was collected with cardiac puncture from all compound treated rats from each group excluding vehicle rats. 0.5 ml of blood was collected with syringe attached to 18 G needle and moved into precooled K2-EDTA microtubes. The EDTA microtube was inverted several times to mix up the EDTA and blood. Tubes were then immediately put on wet ice and centrifuged (Heraeus Fresco 17) within 10-15 minutes of collecting (9.6×1000 G/10×1000 RPM, +4° C. for 2 min), and 200 μl of plasma was collected in 96-tube plates (Matrix Technologies ScreenMates 0.75 ml Alphanumeric Round-Bottom Storage tubes, PP) on dry ice according to sample map.

After collection of blood, the neck was dislocated at the base of the skull. Brain was collected and weighed. Brain weights were recorded and the brain was frozen on dry ice on the 24 well plate.

The plasma and brain samples were stored at −80° C. on dry ice until sent for analysis.

Study 1
Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (−)-α-DHTBZ 2.5 mg/kg (t=0 min) and Amphetamine (t=30 min)
Group 4: 10 rats treated with risperidone 1 mg/kg (t=0 min) and Amphetamine (t=30 min)
Results
1. Distance Travelled Rats dosed with either vehicle, (−)-α-DHTBZ 2.5 mg/kg or risperidone 1 mg/kg were subjected to LMA testing first for 30 minutes and then for 60 minutes after vehicle or amphetamine challenge. Resulting locomotor activity was evaluated in 3 minute bins and as a total over the testing period. The normalised total distance travelled over the testing time is presented in FIG. 1.

When compared to the vehicle-vehicle group the vehicle-amphetamine and (−)-α-DHTBZ 2.5 mg/kg were significantly different. When compared to vehicle-amphetamine group the vehicle-vehicle and risperidone 1 mg/kg were significantly different.

2. Stereotypic Behaviour

Figure 2:
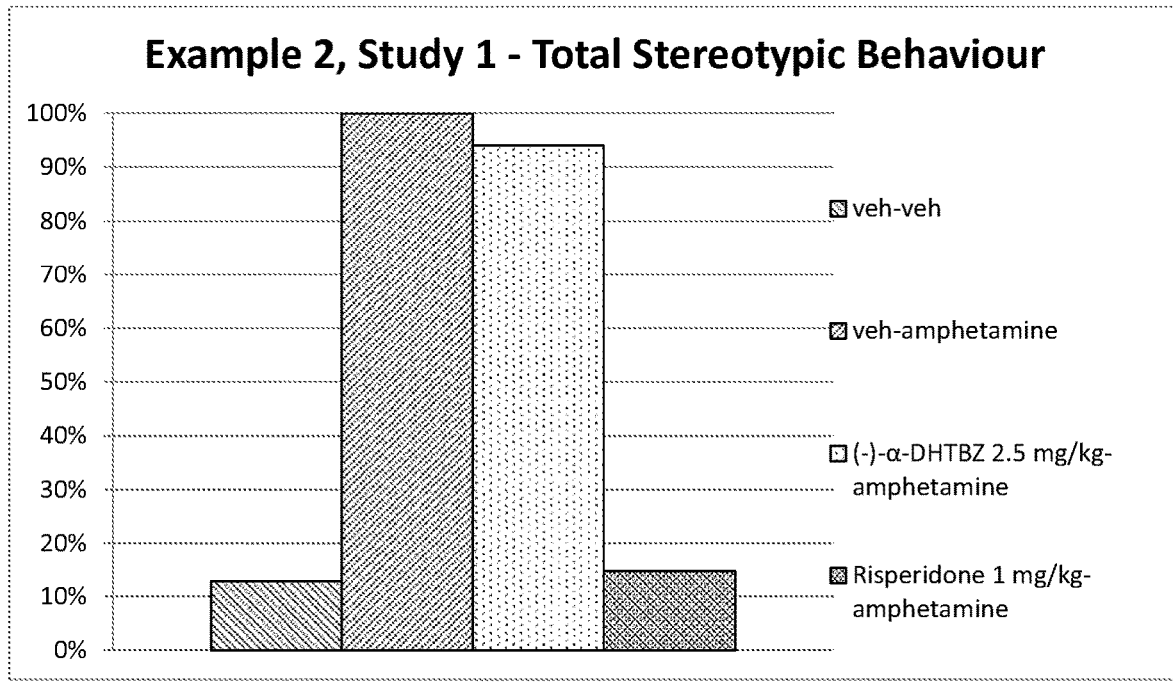
FIG. 2 shows the average total stereotypic behaviour by rats when treated with vehicle (with or without amphetamine induction) and (−)-α-dihydrotetrabenazine at a dose of 2.5 mg/kg and risperidone at a dose of 1 mg/kg in amphetamine-induced rats, as described in Example 2, Study 1 below.

Rats dosed with either vehicle, (−)-α-DHTBZ 2.5 mg/kg or risperidone 1 mg/kg were subjected to LMA testing first for 30 minutes and then for 60 minutes after vehicle or amphetamine challenge. Resulting stereotypic activity was evaluated in 3 minute bins and as a total over the testing period. The normalised total stereotypic behavior over the testing time is presented in FIG. 2.

When compared to the vehicle-vehicle group the vehicle-amphetamine and (−)-α-DHTBZ 2.5 mg/kg were significantly different. When compared to vehicle-amphetamine group, the vehicle-vehicle and risperidone 1 mg/kg were significantly different.

Study 2

The effects on stereotypic behaviour and the distance travelled in rats following administration of (+)-α-dihydrotetrabenazine dosed at 0.1 mg/kg to 0.25 mg/kg, as well as risperidone at 1 mg/kg, were studied.

Figure 3:
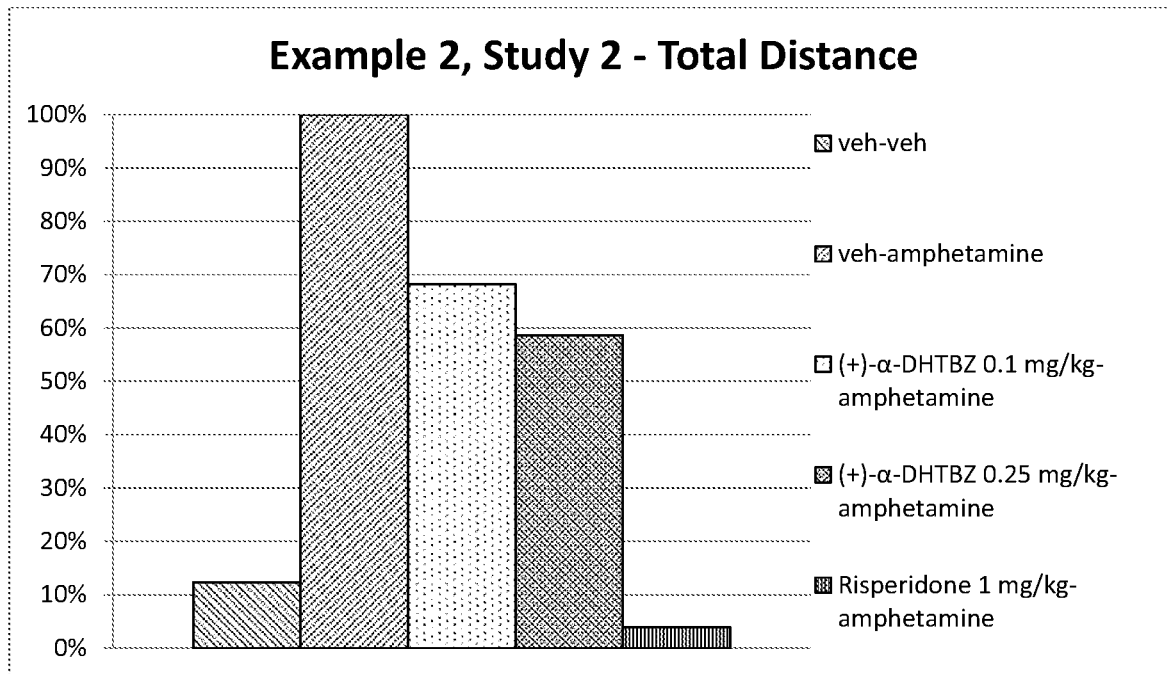
FIG. 3 shows the average total distance travelled by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 2, Study 2 below.

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 0.1 mg/kg (t=0 min) and Amphetamine (t=30 min)
Group 4: 10 rats treated with (+)-α-DHTBZ 0.25 mg/kg (t=0 min) and Amphetamine (t=30 min)
Group 5: 10 rats treated with risperidone 1 mg/kg (t=0 min) and Amphetamine (t=30 min)
Results
1 Distance Travelled Rats dosed with either vehicle, (+)-α-DHTBZ 0.1 mg/kg, (+)-α-DHTBZ 0.25 mg/kg, or risperidone 1 mg/kg were subjected to LMA testing first for 30 minutes and then for 60 minutes after vehicle or amphetamine challenge. Resulting locomotor activity was evaluated in 3 minute bins and as a total over the testing period. The normalised total distance travelled over the testing time is presented in FIG. 3.

When compared to vehicle-amphetamine group the vehicle-vehicle, (+)-α-DHTBZ 0.25 mg/kg and risperidone 1 mg/kg were significantly different.

2 Stereotypic Behaviour

Figure 4:
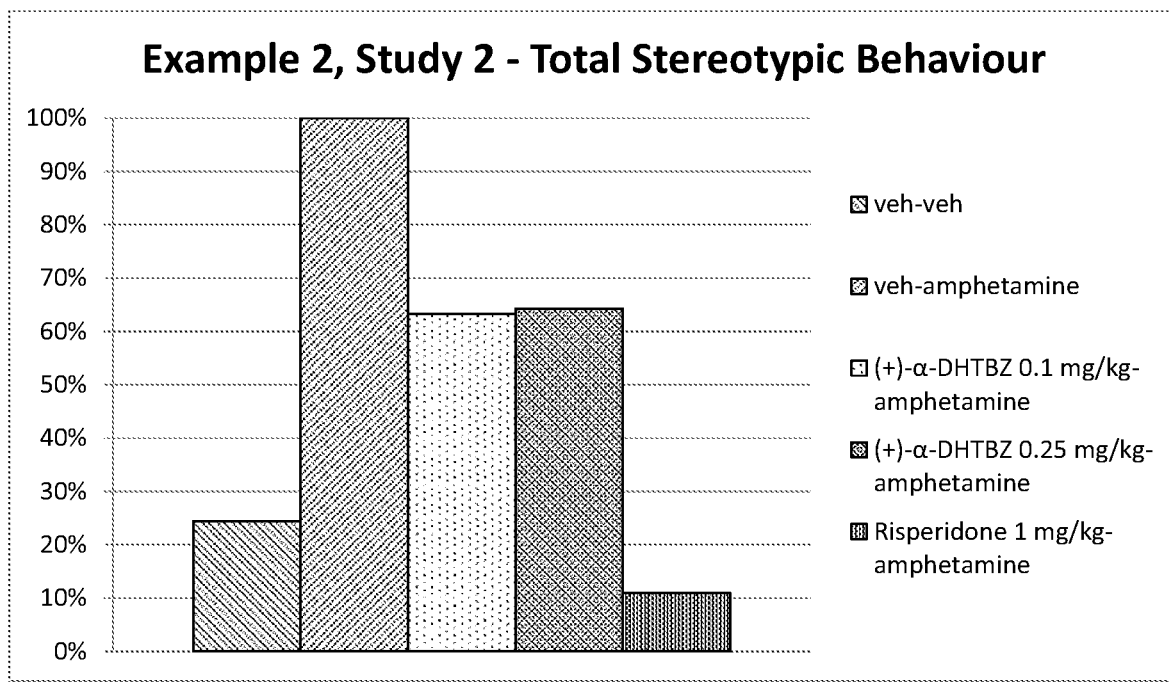
FIG. 4 shows the average total stereotypic behaviour by rats when treated with vehicle (with or without amphetamine induction) and (+)-α-dihydrotetrabenazine at doses of 0.1 mg/kg and 0.25 mg/kg and risperidone at a dose of 1 mg/kg in amphetamine-induced rats, as described in Example 2, Study 2 below.

Rats dosed with either vehicle, (+)-α-DHTBZ 0.1 mg/kg, (+)-α-DHTBZ 0.25 mg/kg, or risperidone 1 mg/kg were subjected to LMA testing first for 30 minutes and then for 60 minutes after vehicle or amphetamine challenge. Resulting stereotypic activity was evaluated in 3 minute bins and as a total over the testing period. The normalised total stereotypic behaviour over the testing time is presented in FIG. 4.

When compared to vehicle-amphetamine group the vehicle-vehicle, (+)-α-DHTBZ 0.1 mg/kg, (+)-α-DHTBZ 0.25 mg/kg and risperidone 1 mg/kg were significantly different.

Figure 5:
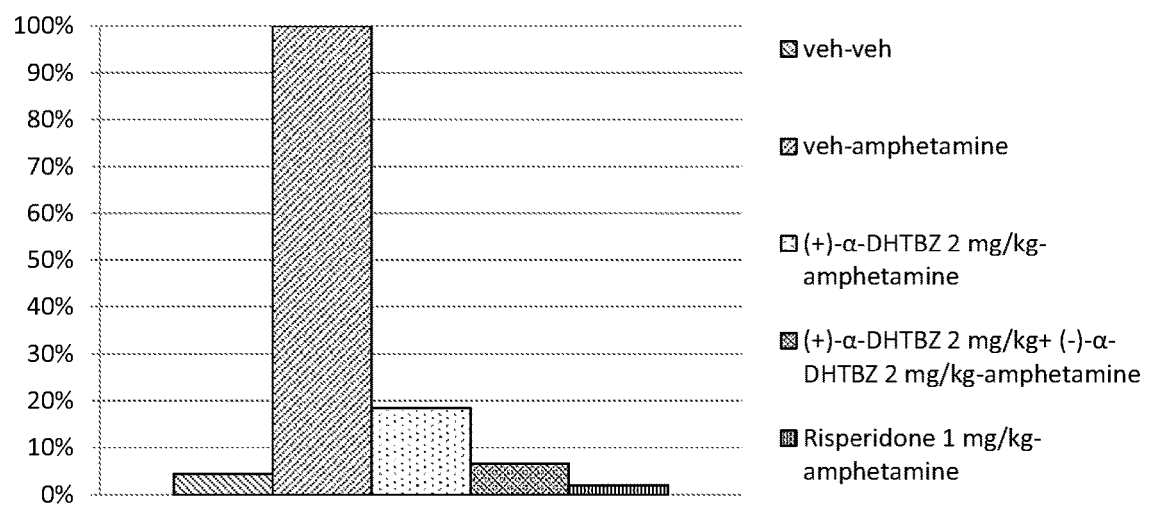
FIG. 5 shows the average total distance travelled by rats when treated with vehicle (with or without amphetamine induction) and (+)-α-dihydrotetrabenazine at a dose of 2 mg/kg, a combination of (+)-α-dihydrotetrabenazine at a dose of 2 mg/kg and (−)-α-dihydrotetrabenazine at a dose of 2 mg/kg, and risperidone at a dose of 1 mg/kg in amphetamine-induced rats, as described in Example 2, Study 3 below.

Study 3
Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 2 mg/kg (t=0 min) and Amphetamine (t=30 min)
Group 4: 10 rats treated with (+)-α-DHTBZ 2 mg/kg with (−)-α-DHTBZ 2 mg/kg (t=0 min) and Amphetamine (t=30 min)
Group 5: 10 rats treated with risperidone 1 mg/kg (t=0 min) and Amphetamine (t=30 min)
Results
1 Distance Travelled Rats dosed with either vehicle, (+)-α-DHTBZ 2 mg/kg, the combination of (−)-α-DHTBZ 2 mg/kg and (+)-α-DHTBZ 2 mg/kg or risperidone 1 mg/kg were subjected to LMA testing first for 30 minutes and then for 60 minutes after vehicle or amphetamine challenge. Resulting locomotor activity was evaluated in 3 minute bins and as a total over the testing period. The normalised total distance travelled over the testing time is presented in FIG. 5.

When compared to the vehicle-vehicle group the vehicle-amphetamine was significantly different. When compared to vehicle-amphetamine group the vehicle-vehicle, (+)-α-DHTBZ 2 mg/kg, the combination of (−)-α-DHTBZ 2 mg/kg and (+)-α-DHTBZ 2 mg/kg and risperidone 1 mg/kg were significantly different.

2 Stereotypic Behaviour

Figure 6:
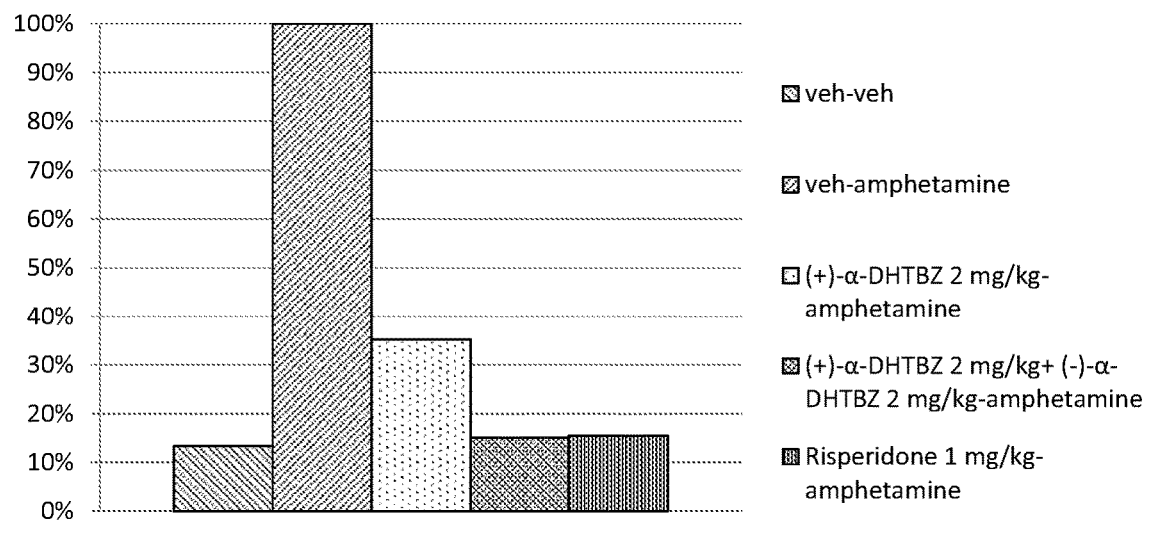
FIG. 6 shows the average total stereotypic behaviour by rats when treated with vehicle (with or without amphetamine induction) and (+)-α-dihydrotetrabenazine at a dose of 2 mg/kg, a combination of (+)-α-dihydrotetrabenazine at a dose of 2 mg/kg and (−)-α-dihydrotetrabenazine at a dose of 2 mg/kg, and risperidone at a dose of 1 mg/kg in amphetamine-induced rats, as described in Example 2, Study 3 below.

Rats dosed with either vehicle, (+)-α-DHTBZ 2 mg/kg, the combination of (−)-α-DHTBZ 2 mg/kg and (+)-α-DHTBZ 2 mg/kg or Risperidone 1 mg/kg were subjected to LMA testing first for 30 min and then for 60 minutes after vehicle or amphetamine challenge. Resulting stereotypic activity was evaluated in 3 min bins and as a total over the testing period. The normalised total stereotypic behaviour over the testing time is presented in FIG. 6.

When compared to vehicle-amphetamine group the vehicle-vehicle, (+)-α-DHTBZ 2 mg/kg, the combination of (−)-α-DHTBZ 2 mg/kg and (+)-α-DHTBZ 2 mg/kg and risperidone 1 mg/kg were significantly different.

Study 4

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 0.5 mg/kg (t=0 min) and (−)-α-DHTBZ 0.5 mg/kg and Amphetamine (t=30 min)
Group 4: 10 rats treated with (+)-α-DHTBZ 1.0 mg/kg (t=0 min) and (−)-α-DHTBZ 0.5 mg/kg and Amphetamine (t=30 min)
Group 5: 10 rats treated with (+)-α-DHTBZ 1.0 mg/kg (t=0 min) and (−)-α-DHTBZ 1.0 mg/kg and Amphetamine (t=30 min)
Group 6: 10 rats treated with (+)-α-DHTBZ 1.5 mg/kg (t=0 min) and (−)-α-DHTBZ 1.0 mg/kg and Amphetamine (t=30 min)

Results

1 Distance Travelled

Figure 7:
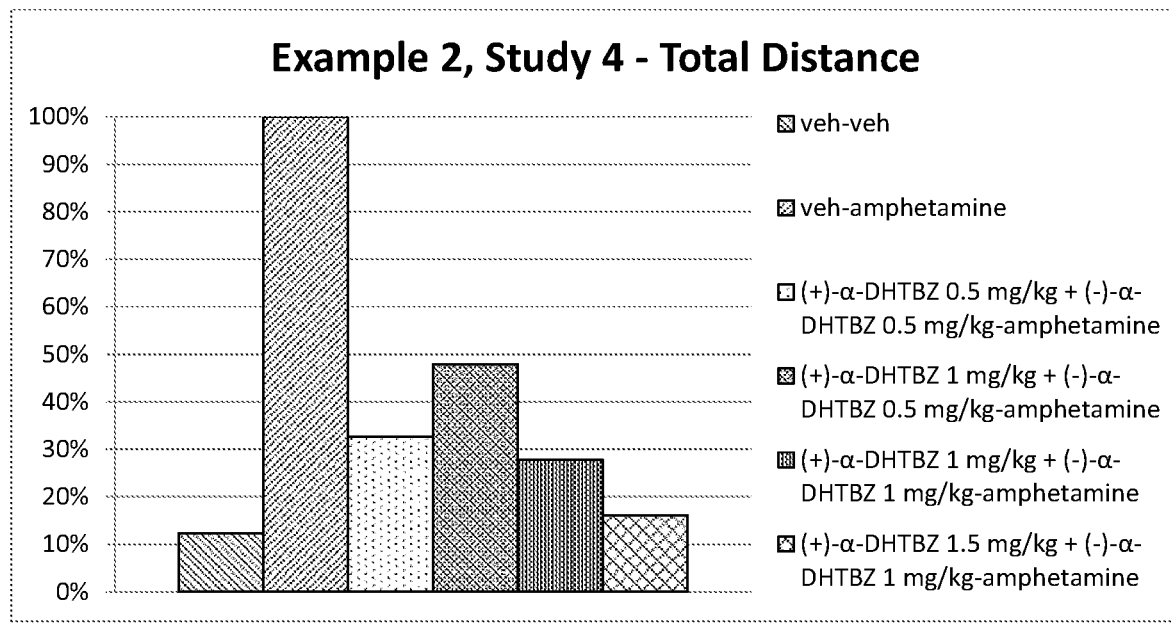
FIG. 7 shows the average total distance travelled by rats when treated with vehicle (with or without amphetamine induction) and combinations of (+)-α-dihydrotetrabenazine and (−)-α-dihydrotetrabenazine in varying ratios, and risperidone at a dose of 1 mg/kg in amphetamine-induced rats, as described in Example 2, Study 4 below.

Rats dosed with either vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg or the combination of (+)-α-DHTBZ 1.5 mg/kg and (−)-α-DHTBZ 1 mg/kg were subjected to LMA testing first for 30 minutes and then for 60 minutes after vehicle or amphetamine challenge. Resulting locomotor activity was evaluated in 3 minute bins and as a total over the testing period. The normalised total distance travelled over the testing time is presented in FIG. 7.

When compared to vehicle-amphetamine group the vehicle-vehicle, (+)-α-DHTBZ, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg and the combination of (+)-α-DHTBZ 1.5 mg/kg and (−)-α-DHTBZ 1 mg/kg were significantly different.

2 Stereotypic Behaviour

Figure 8:
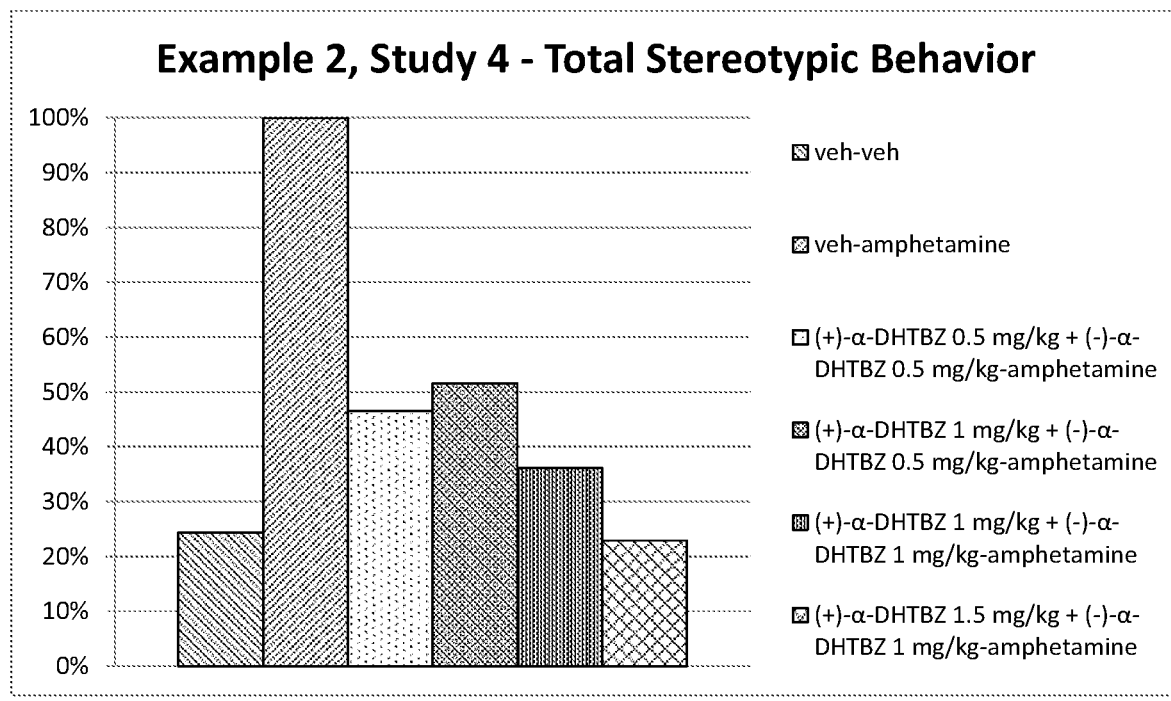
FIG. 8 shows the average total stereotypic behaviour by rats when treated with vehicle (with or without amphetamine induction) and combinations of (+)-α-dihydrotetrabenazine and (−)-α-dihydrotetrabenazine in varying ratios, and risperidone at a dose of 1 mg/kg in amphetamine-induced rats, as described in Example 2, Study 4 below.

Rats dosed with either vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg or the combination of (+)-α-DHTBZ 1.5 mg/kg and (−)-α-DHTBZ 1 mg/kg were subjected to LMA testing first for 30 min and then for 60 minutes after vehicle or amphetamine challenge. Resulting stereotypic activity was evaluated in 3 minute bins and as a total over the testing period. The normalised total stereotypic behaviour over the testing time is presented in FIG. 8.

When compared to the vehicle-vehicle group the combination of (+)-α-DHTBZ 1 mg/kg and (−)-α-DHTBZ 0.5 mg/kg was significantly different. When compared to vehicle-amphetamine group the vehicle-vehicle, the combination of (+)-α-DHTBZ 0.5 mg/kg and (−)-α-DHTBZ 0.5 mg/kg, the combination of (+)-α-DHTBZ 1 mg/kg and (−)-α-DHTBZ 0.5 mg/kg, the combination of (+)-α-DHTBZ 1 mg/kg and (−)-α-DHTBZ 1 mg/kg and the combination of (+)-α-DHTBZ 1.5 mg/kg and (−)-α-DHTBZ 1 mg/kg were significantly different.

Study 5

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-β-DHTBZ 2.5 mg/kg (t=0 min) and Amphetamine (t=30 min)
Group 4: 10 rats treated with (+)-β-DHTBZ 5 mg/kg (t=0 min) and Amphetamine (t=30 min)
Group 5: 10 rats treated with and (+)-β-DHTBZ 2.5 mg/kg and (+)-α-DHTBZ 2.5 mg/kg (t=0 min) and Amphetamine (t=30 min)

Results

1 Distance Travelled

Figure 9:
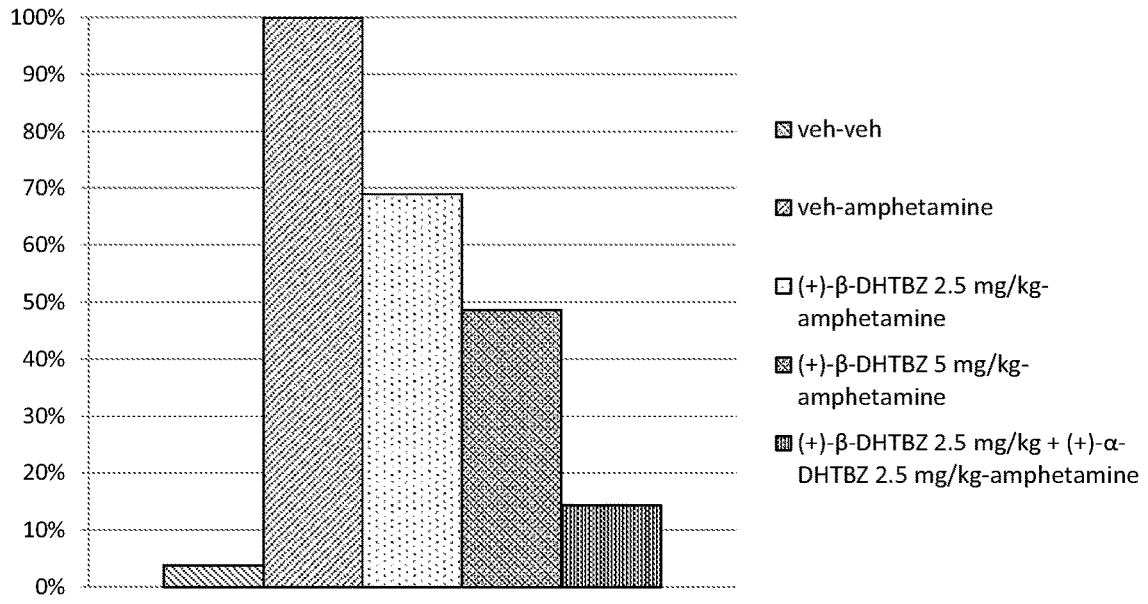
FIG. 9 shows the average total distance travelled by rats when treated with vehicle (with or without amphetamine induction), (+)-β-dihydrotetrabenazine and combinations of (+)-α-dihydrotetrabenazine and (+)-β-dihydrotetrabenazine in amphetamine-induced rats, as described in Example 2, Study 5 below.

Rats dosed with either vehicle, (+)-β-DHTBZ 2.5 mg/kg, (+)-β-DHTBZ 5 mg/kg or (+)-β-DHTBZ 2.5 mg/kg and (+)-α-DHTBZ 2.5 mg/kg were subjected to LMA testing first for 30 minutes and then for 60 minutes after vehicle or amphetamine challenge. Resulting locomotor activity was evaluated in 3 minute bins and as a total over the testing period. The normalised total distance travelled over the testing time is presented in FIG. 9.

When compared to the vehicle-vehicle group the vehicle-amphetamine, (+)-β-DHTBZ 2.5 mg/kg and (+)-β-DHTBZ 5 mg/kg. When compared to vehicle-amphetamine group the vehicle-vehicle, the combination of (+)-β-DHTBZ 2.5 mg/kg and (+)-α-DHTBZ 2.5 mg/kg, (+)-β-DHTBZ 2.5 mg/kg and (+)-β-DHTBZ 5 mg/kg, were significantly different.

2 Stereotypic Behaviour

Figure 10:
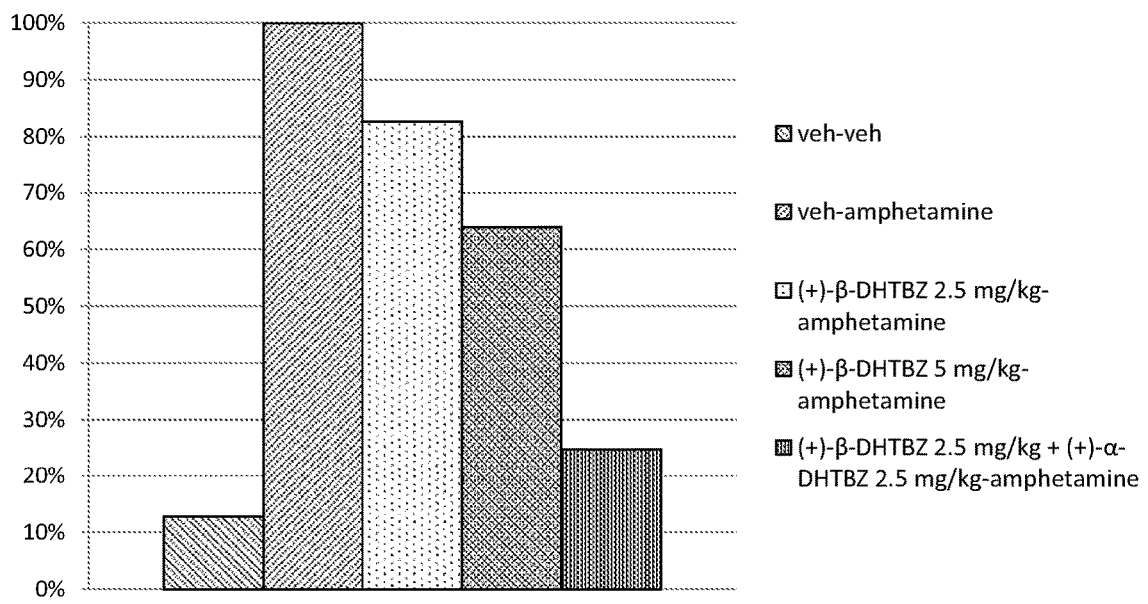
FIG. 10 shows the average total stereotypic behaviour by rats when treated with vehicle (with or without amphetamine induction), (+)-β-dihydrotetrabenazine and combinations of (+)-α-dihydrotetrabenazine and (+)-β-dihydrotetrabenazine in amphetamine-induced rats, as described in Example 2, Study 5 below.

Rats dosed with either vehicle, (+)-β-DHTBZ 2.5 mg/kg, (+)-β-DHTBZ 5 mg/kg or (+)-β-DHTBZ 2.5 mg/kg and (+)-α-DHTBZ 2.5 mg/kg were subjected to LMA testing first for 30 minutes and then for 60 minutes after vehicle or amphetamine challenge. Resulting stereotypic activity was evaluated in 3 minute bins and as a total over the testing period. The normalised total stereotypic behaviour over the testing time is presented in FIG. 10.

When compared to the vehicle-vehicle group the vehicle-amphetamine, (+)-β-DHTBZ 2.5 mg/kg and (+)-β-DHTBZ 5 mg/kg were significantly different. When compared to vehicle-amphetamine group the vehicle-vehicle, the combination of (+)-β-DHTBZ 2.5 mg/kg and (+)-α-DHTBZ 2.5 mg/kg, (+)-β-DHTBZ 2.5 mg/kg and (+)-β-DHTBZ 5 mg/kg were significantly different.

Study 6

Animals were grouped as follows:
Group 1: 10 rats treated with Vehicle (t=0 min) and Vehicle (t=30 min)
Group 2: 10 rats treated with Vehicle (t=0 min) and Amphetamine (t=30 min)
Group 3: 10 rats treated with (+)-α-DHTBZ 1 mg/kg (t=0 min) and amphetamine (t=30 min)

Group 4: 10 rats treated with (+)-α-DHTBZ 1 mg/kg plus (−)-α-DHTBZ 1 mg/kg (t=0 min); and amphetamine (t=30 min)

Group 5: 10 rats treated with (+)-α-DHTBZ 1 mg/kg plus (−)-β-DHTBZ 1 mg/kg (t=0 min) and t=30 min)amphetamine Group 6: 10 rats treated with (+)-β-DHTBZ 1 mg/kg plus (−)-α-DHTBZ 1 mg/kg (t=0 min); and amphetamine (t=30 min)

Group 7: 10 rats treated with (+)-β-DHTBZ 1 mg/kg plus (−)-β-DHTBZ 1 mg/kg (t=0 min); and amphetamine (t=30 min)

Group 8: 10 rats treated with (+)-α-DHTBZ 1 mg/kg plus (+)-β-DHTBZ 1 mg/kg (t=0 min); and amphetamine (t=30 min)

Group 9: 10 rats treated with risperidone 1 mg/kg (t=0 min); and amphetamine (t=30 min)

Results

1 Distance Travelled

Figure 11:
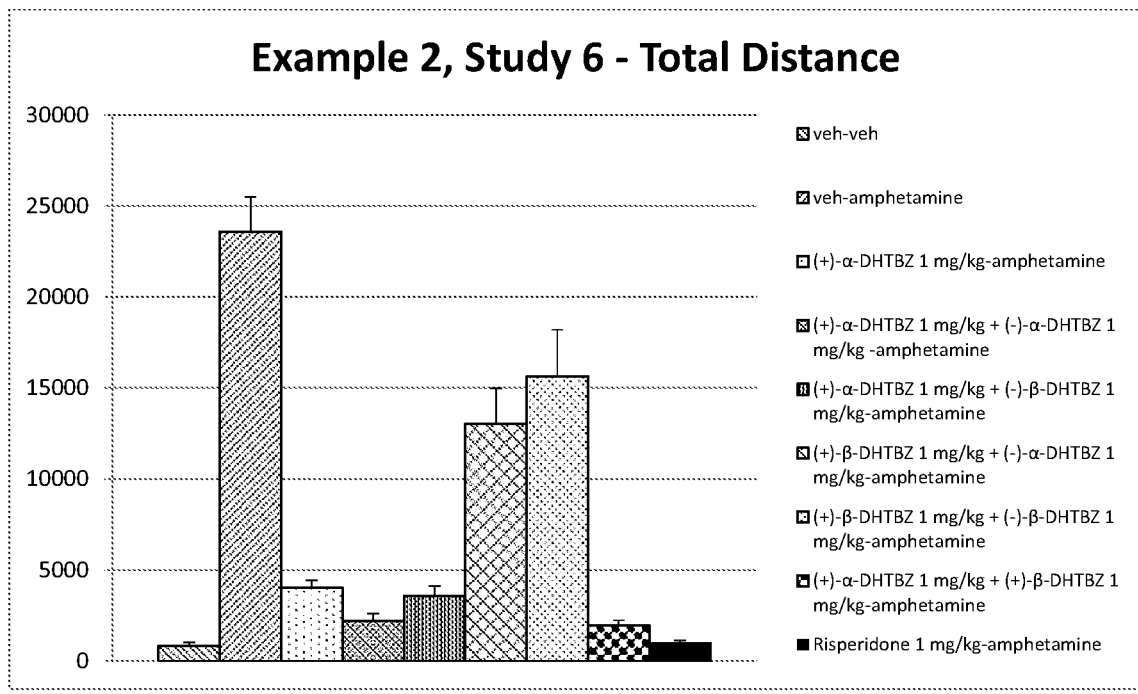
FIG. 11 shows the average total distance travelled by rats when treated with vehicle (with or without amphetamine induction), (+)-α-dihydrotetrabenazine alone, (+)-α-dihydrotetrabenazine in combination with (−)-β-dihydrotetrabenazine, (+)-β-dihydrotetrabenazine in combination with (−)-α-dihydrotetrabenazine, (+)-β-dihydrotetrabenazine in combination with (−)-β-dihydrotetrabenazine, and (+)-α-dihydrotetrabenazine in combination with (+)-β-dihydrotetrabenazine in amphetamine-induced rats, as described in Example 2, Study 6 below.

Rats dosed with either vehicle or dihydrotetrabenazine were subjected to LMA testing first for 30 minutes and then for 60 minutes after vehicle or amphetamine challenge. Resulting locomotor activity was evaluated in 3 minute bins and as a total over the testing period. The unnormalised total distance travelled over the testing time is presented in FIG. 11.

When compared to the vehicle-vehicle group, the vehicle-amphetamine, (+)-β-DHTBZ 1 mg/kg plus (−)-α-DHTBZ 1 mg/kg and (+)-β-DHTBZ 1 mg/kg plus (−)-β-DHTBZ 1 mg/kg groups were significantly different. When compared to the vehicle-amphetamine group, the vehicle-vehicle, all of groups 1 and 3 to 9 were significantly different.

2 Stereotypic Behaviour

Figure 12:
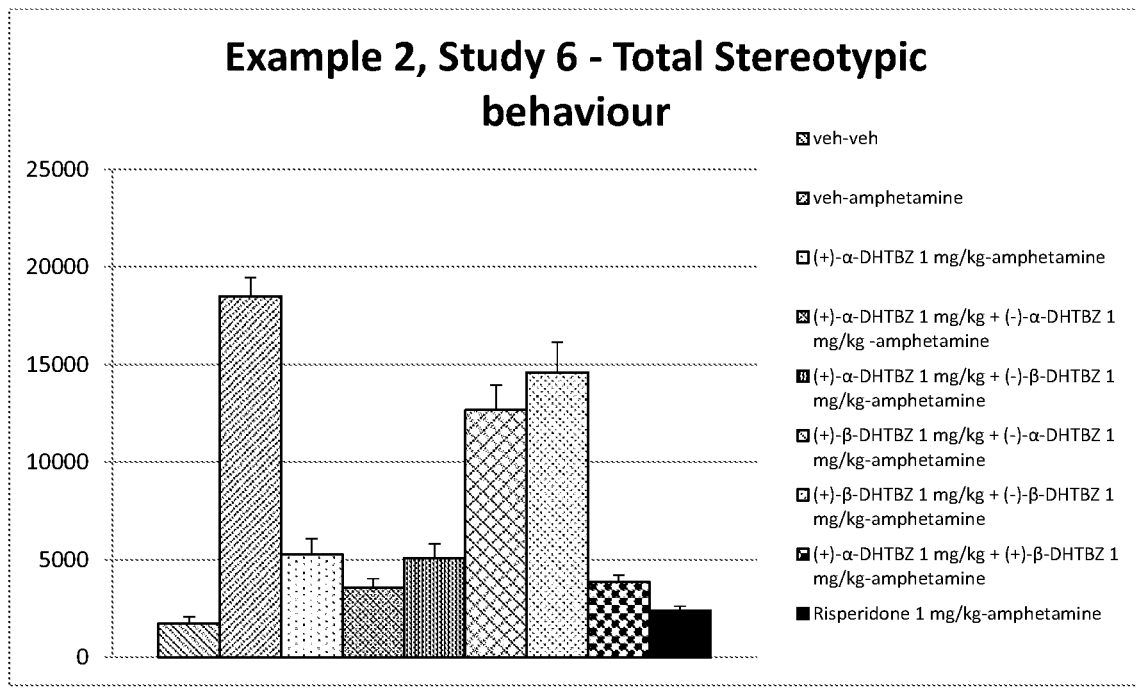
FIG. 12 shows the stereotypic behaviour (distance over time) by rats when treated with vehicle (with or without amphetamine induction), (+)-α-dihydrotetrabenazine alone, (+)-α-dihydrotetrabenazine in combination with (−)-β-dihydrotetrabenazine, (+)-β-dihydrotetrabenazine in combination with (−)-α-dihydrotetrabenazine, (+)-β-dihydrotetrabenazine in combination with (−)-β-dihydrotetrabenazine, and (+)-α-dihydrotetrabenazine in combination with (+)-β-dihydrotetrabenazine in amphetamine-induced rats, as described in Example 2, Study 6 below.

Rats dosed with either vehicle or dihydroterabenazine were subjected to LMA testing first for 30 minutes and then for 60 minutes after vehicle or amphetamine challenge. Resulting stereotypic activity was evaluated in 3 minute bins and as a total over the testing period. The unnormalised total stereotypic behaviour over the testing time is presented in FIG. 12.

When compared to the vehicle-vehicle group, the vehicle-amphetamine, (+)-β-DHTBZ 1 mg/kg plus (−)-α-DHTBZ 1 mg/kg and (+)-β-DHTBZ 1 mg/kg plus (−)-β-DHTBZ 1 mg/kg groups were significantly different. When compared to the vehicle-amphetamine group, the vehicle-vehicle, all of groups 1 and 3 to 9 were significantly different.

CONCLUSIONS

Study 1 evaluated the effect of (−)-α-DHTBZ at a dose of 2.5 mg/kg and risperidone at a dose of 1 mg/kg on amphetamine induced locomotor activity in male CD rats.

(−)-α-DHTBZ at a dose of 2.5 mg/kg did not lead to lower locomotor activity or reduced stereotypic behaviour when compared to the vehicle-amphetamine group. The rats dosed with (−)-α-DHTBZ at a dose of 2.5 mg/kg were less focused on what was going on around them. The rats dosed with (−)-α-DHTBZ were equally active when compared to the vehicle-amphetamine dosed animals suggesting that (−)-α-DHTBZ does not have an effect on movement similar to risperidone.

Study 2 evaluated the effect of (+)-α-DHTBZ at doses 0.1 mg/kg and 0.25 mg/kg and risperidone at dose 1 mg/kg on amphetamine induced locomotor activity in male CD rats.

(+)-α-DHTBZ at 0.25 mg/kg and risperidone 1 mg/kg led to lower locomotor activity when compared to the vehicle-amphetamine group. (+)-α-DHTBZ at both the tested doses and risperidone 1 mg/kg led to reduced stereotypic behaviour when compared to the vehicle-amphetamine group.

Study 3 evaluated the effect of (+)-α-DHTBZ at a dose of 2 mg/kg, the combination of (+)-α-DHTBZ and (−)-α-DHTBZ at dose 2 mg/kg and risperidone at dose 1 mg/kg on amphetamine induced locomotor activity in male CD rats.

(+)-α-DHTBZ at all the tested dose, the combination of (+)-α-DHTBZ and (−)-α-DHTBZ at doses of 2 mg/kg and risperidone at 1 mg/kg led to lower locomotor activity when compared to the vehicle-amphetamine group. (+)-α-DHTBZ at all the tested dose, the combination of (+)-α-DHTBZ and (−)-α-DHTBZ at doses of 2 mg/kg and risperidone 1 mg/kg led to reduced stereotypic behaviour when compared to the vehicle-amphetamine group.

Amphetamine induced locomotor activity was less in rats treated with the combination of (+)-α-DHTBZ and (−)-α-DHTBZ than in rats treated with (+)-α-DHTBZ only, despite it being shown that the (−)-α-isomer provides very little, if any, reduction in induced locomotor activity.

Study 4 evaluated the effect of the combination of (+)-α-DHTBZ and (−)-α-DHTBZ at doses 0.5 mg/kg+0.5 mg/kg, 1 mg/kg+0.5 mg/kg, 1 mg/kg+1 mg/kg and 1.5 mg/kg+1 mg/kg on amphetamine induced locomotor activity in male CD rats.

The combination of (+)-α-DHTBZ and (−)-α-DHTBZ at all the tested combinations and risperidone 1 mg/kg led to lower locomotor activity when compared to the vehicle-amphetamine group. The combination of (+)-α-DHTBZ and (−)-α-DHTBZ at all the tested doses and risperidone 1 mg/kg led to reduced stereotypic behaviour when compared to the vehicle-amphetamine group.

Comparing the data for rats dosed with a combination of (+)-α-DHTBZ at a dose of 1 mg/kg and (−)-α-DHTBZ at a dose of 0.5 mg/kg and rats dosed with a combination of (+)-α-DHTBZ at a dose of 1 mg/kg and (−)-α-DHTBZ at a dose of 1 mg/kg, given the demonstrated lack of efficiency of the (−)-α-isomer in isolation, it was surprising that increasing the amount of (−)-α-isomer in the combination treatment led to a reduction in the locomotor activity in the tested rats.

Study 5 evaluated the effect of (+)-β-DHTBZ at doses 2.5 mg/kg and 5 mg/kg and the combination of (+)-α-DHTBZ at dose 2.5 mg/kg and (+)-β-DHTBZ at dose 2.5 mg/kg on amphetamine induced locomotor activity in male CD rats.

(+)-β-DHTBZ 2.5 mg/kg, (+)-β-DHTBZ 5 mg/kg, and the combination of (+)-α-DHTBZ 2.5 mg/kg and (+)-β-DHTBZ 2.5 mg/kg led to lower locomotor activity when compared to the vehicle-amphetamine group. (+)-β-DHTBZ 2.5 mg/kg, (+)-β-DHTBZ 5 mg/kg and the combination of (+)-α-DHTBZ 2.5 mg/kg and (+)-β-DHTBZ 2.5 mg/kg also led to reduced stereotypic behaviour when compared to the vehicle-amphetamine group. The rats dosed with (+)-β-DHTBZ at dose 5 mg/kg were less focused on what was going on around them and the rats that received the (+)-β-DHTBZ 5 mg/kg were observed to have tensed limbs and were partially missing their righting reflex at the end of the test.

Study 6 evaluated the effect of (+)-α-DHTBZ at a dose of 1 mg/kg, a combination of (+)-α-DHTBZ at a dose of 1 mg/kg plus (−)-α-DHTBZ at a dose of 1 mg/kg, a combination of (+)-α-DHTBZ at a dose of 1 mg/kg plus (−)-β-DHTBZ at a dose of 1 mg/kg, a combination of (+)-β-DHTBZ at a dose of 1 mg/kg plus (−)-α-DHTBZ at a dose of 1 mg/kg, a combination of (+)-β-DHTBZ at a dose of 1 mg/kg plus (−)-β-DHTBZ at a dose of 1 mg/kg, a combination of (+)-α-DHTBZ at a dose of 1 mg/kg plus (+)-β-

DHTBZ at a dose of 1 mg/kg, and risperidone at a dose of 1 mg/kg (t=0 min) on amphetamine induced locomotor activity in male CD rats.

The vehicle, risperidone and all of the dihydrotetrabenazine-containing led to lower locomotor activity and led to reduced stereotypic behaviour when compared to the vehicle-amphetamine group.

The results obtained from the six studies indicate that combinations of (+)-β-dihydrotetrabenazine, (−)-α-dihydrotetrabenazine and (+)-α-dihydrotetrabenazine will be useful in the treatment of movement disorders.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A pharmaceutical combination comprising:
   (a) (+)-β-dihydrotetrabenazine, or a pharmaceutically acceptable salt thereof;
   (b) (−)-α-dihydrotetrabenazine, or a pharmaceutically acceptable salt thereof; and
   (c) (+)-α-dihydrotetrabenazine, or a pharmaceutically acceptable salt thereof.

2. A pharmaceutical combination according to claim 1 which comprises from 35 to 75 parts by weight of (+)-β-dihydrotetrabenazine and from 25 to 55 parts by weight of a mixture of (+)-α-dihydrotetrabenazine and (−)-α-dihydrotetrabenazine.

3. A pharmaceutical combination according to claim 1 comprising:
   (a) 40-65 parts by weight of (+)-β-dihydrotetrabenazine, or a pharmaceutically acceptable salt thereof; and
   (c) 40-65 parts by weight of (+)-α-dihydrotetrabenazine, or a pharmaceutically acceptable salt thereof.

4. A pharmaceutical combination according to claim 3 comprising:
   (a) 45-55 parts by weight of (+)-β-dihydrotetrabenazine, or a pharmaceutically acceptable salt thereof; and
   (c) 45-55 parts by weight of (+)-α-dihydrotetrabenazine, or a pharmaceutically acceptable salt thereof.

5. A pharmaceutical combination according to claim 2 which comprises:
   (a) 45-65 parts by weight of (+)-β-dihydrotetrabenazine, or a pharmaceutically acceptable salt thereof;
   (b) 30-50 parts by weight of (−)-α-dihydrotetrabenazine, or a pharmaceutically acceptable salt thereof; and optionally
   (c) 0.1-5 parts by weight of (+)-α-dihydrotetrabenazine, or a pharmaceutically acceptable salt thereof.

6. A pharmaceutical unit dosage form comprising a pharmaceutically acceptable excipient and a pharmaceutical combination as defined in claim 1.

7. A pharmaceutical unit dosage form according to claim 6 wherein the sum of the amounts of (+)-β-dihydrotetrabenazine, (−)-α-dihydrotetrabenazine and (+)-α-dihydrotetrabenazine does not exceed 100 mg.

8. A pharmaceutical unit dosage form according to claim 6 which is selected from capsules and tablets.

9. A pharmaceutical combination according to claim 1 wherein the combination is substantially free of (−)-β-dihydrotetrabenazine.

10. A pharmaceutical combination according to claim 1 wherein the combination contains less than 3% of (−)-β-dihydrotetrabenazine by weight compared to the total weight of all isomers of dihydrotetrabenazine present.

11. A pharmaceutical unit dosage form according to claim 6 wherein the combination is substantially free of (−)-β-dihydrotetrabenazine.

12. A pharmaceutical unit dosage form according to claim 6 wherein the combination contains less than 3% of (−)-β-dihydrotetrabenazine by weight compared to the total weight of all isomers of dihydrotetrabenazine present.

* * * * *